US011058734B2

(12) United States Patent
Sañudo Otero et al.

(10) Patent No.: US 11,058,734 B2
(45) Date of Patent: Jul. 13, 2021

(54) PROBIOTIC STRAINS HAVING CHOLESTEROL ABSORBING CAPACITY, METHODS AND USES THEREOF

(71) Applicant: BIOSEARCH, S.A., Granada (ES)

(72) Inventors: Ana Isabel Sañudo Otero, Dueñas-Palencia (ES); Raquel Criado García, Madrid (ES); Alba Rodríguez Nogales, Pedrera-Sevilla (ES); Alberto Garach Domech, Granada (ES); Mónica Olivares Martín, Huetor Vega-Granada (ES); Julio Juan Gálvez Peralta, Granada (ES); Santiago De La Escalera Huerso, Granada (ES); Juan Manuel Duarte Pérez, Granada (ES); Antonio Zarzuelo Zurita, Granada (ES); Óscar Bañuelos Hortigüela, Cúllar Vega-Granada (ES)

(73) Assignee: BIOSEARCH, S.A., Granada (ES)

( * ) Notice: Subject to any disclaimer, the term of this patent is extended or adjusted under 35 U.S.C. 154(b) by 179 days.

(21) Appl. No.: 15/534,059

(22) PCT Filed: Dec. 10, 2015

(86) PCT No.: PCT/EP2015/079298
§ 371 (c)(1),
(2) Date: Jun. 8, 2017

(87) PCT Pub. No.: WO2016/092032
PCT Pub. Date: Jun. 16, 2016

(65) Prior Publication Data
US 2017/0333495 A1 Nov. 23, 2017

(30) Foreign Application Priority Data
Dec. 10, 2014 (EP) .................................. 14384202

(51) Int. Cl.
*A61K 35/745* (2015.01)
*A61K 35/747* (2015.01)
*C12R 1/01* (2006.01)
*C12R 1/225* (2006.01)
*A61K 35/00* (2006.01)

(52) U.S. Cl.
CPC .......... *A61K 35/747* (2013.01); *A61K 35/745* (2013.01); *C12R 1/01* (2013.01); *C12R 1/225* (2013.01); *A61K 2035/115* (2013.01)

(58) Field of Classification Search
None
See application file for complete search history.

(56) References Cited

U.S. PATENT DOCUMENTS

2010/0074933 A1* 3/2010 Prakash .................. C12N 11/02
424/422

FOREIGN PATENT DOCUMENTS

WO 02/027016 A2 4/2002
WO WO-2012153179 A1 * 11/2012 ............. A23L 29/25

OTHER PUBLICATIONS

Miremadi et al., "Cholesterol Reduction Mechanisms and Fatty Acid Composition of Cellular Membranes of Probiotic Lactobacilli and Bifidobacteria", Journal of Functional Foods, Jul. 1, 2014, pp. 295-305, vol. 9.
Hong-Sup et al., "Reduction in Cholesterol Absoption in Caco-2 Cells Through the Down-Regulation of Niemann-Pick C1-like 1 by the Putative Probiotic Strains Lactobacillus Plantarum NR74 from Fermented", International Journal of Food Sciences and Nutirition, Feb. 1, 2013, pp. 44-52, No. 1, Carefax Publishing Ltd., United Kingdom.
Tok et al., "Cholesterol Removal by Some Lactic Acid Bacteria That Can be Used as Probiotic", Microbiology and Immunology, Mar. 1, 2010, pp. 257-264, vol. 54.
Bordoni et al., "Cholestrol-Lowering Probiotics: In Vitro Selection and in Vivo Testing of Bifidobacteria", Applied Microbiology and Biotechnology, Jul. 20, 2013, pp. 8273-8281, vol. 97, No. 18.
Bohlin et al., "Reliability and Applications of Statistical Methods Based on Oligonucleotide Frequencies in Bacterial and Archaeal Genomes", BMC Genomics, Feb. 28, 2008, pp. 1-18, vol. 9, No. 104.
Bouchet et al., "Molecular Genetics Basis of Ribotyping", Clinical Microbiology Reviews, Apr. 2008, pp. 262-273, vol. 21, No. 2.
Chomczynski et al., "Single-Step Method of RNA Isolation by Acid Guanidinium Thiocyanate-Phenol-Chloroform Extraction", Analytical Biochemistry, 1987, pp. 156-159, vol. 162.
Chou et al., "Genetic Relatedness Between Listeria monocytogenes Isolates from Seafood and Humans Using PFGE and REP-PCR", International Journal of Food Microbiology, 2006, pp. 135-148, vol. 110.
European Search Report for EP Application 14384202.9 dated Jun. 11, 2015.
International Search Report and Written Opinion for PCT/EP2015/079298 dated Feb. 12, 2016.

(Continued)

*Primary Examiner* — Soren Harward
*Assistant Examiner* — Paul D Pyla
(74) *Attorney, Agent, or Firm* — Thompson Coburn LLP; William A. Holtz

(57) ABSTRACT

The invention relates to a probiotic strain selected from *Lactobacillus reuteri* V340 with accession number CECT and *Bifidobacterium breve* BT820 with accession number CECT 8606, or a variant of said probiotic strain having cholesterol-absorbing capacity, and to methods and therapeutic uses thereof. The invention also relates to compositions, pharmaceutical compositions, feeds or nutritional products comprising a probiotic strain selected from *Lactobacillus reuteri* V3401 with accession number CECT 8605 and *Bifidobacterium breve* BT820 with accession number CECT 8606, or a variant of said probiotic strain having cholesterol-absorbing capacity.

8 Claims, 13 Drawing Sheets
Specification includes a Sequence Listing.

(56) References Cited

OTHER PUBLICATIONS

Konstantinos et al., "Genomic Insights that Advance the Species Definition for Prokaryotes", Proceedings of the National Academy of Sciences, Feb. 15, 2005, pp. 2567-2572, vol. 102, No. 7.
Maiden et al., "Multilocus Sequence Typing: A Portable Approach to the Identification of Clones within Populations of Pathogenic Microorganisms", Proceedings of the National Academy of Sciences, Mar. 1998, pp. 3140-3145, vol. 95.
Malinicova et al., "Peptidoglycan Hydrolases as Novel Tool for Anti-Enterococcal Therapy", Current Research, Technology and Education Topics in Applied Microbiology and Microbial Biotechnology, 2010, pp. 463-472.
Sparrow et al., "A Fluorescent Cholesterol Analog Traces Cholesterol Absorption in Hamsters and is Esterified in Vivo and in Vitro", Journal of Lipid Research, 1999, pp. 1747-1757, vol. 40.
Vollmer et al., "Bacterial Peptidoglycan (murein) Hydrolases". FEMS Microbiology Reviews, 2008, pp. 259-286, vol. 32.
Willems et al., "Standardization of Real-Time PCR Gene Expression Data from Independent Biological Replicates", Analytical Biochemistry, 2008, pp. 127-129, vol. 379.
Tomaro-Duchesneau et al., "Cholesterol Assimilation by Lactobacillus Probiotic Bacteria: An In Vitro Investigation", BioMed Research International, Sep. 11, 2014, pp. 1-9, vol. 2014, Article ID 380316.
Lisman et al., "Binding of Cholesterol to the cells and peptidoglycan of Lactobacillus gasseri", Milchwissenschaft, 1999, pp. 495-498, vol. 54, No. 9.
Rodes et al., "Design of a novel gut bacterial adhesion model for probiotic applications", Artificial Cells, Nanomedicine, and Biotechnology, 2013, pp. 116-124, vol. 41.

\* cited by examiner

A

B

PROBIOTIC STRAINS HAVING CHOLESTEROL ABSORBING CAPACITY, METHODS AND USES THEREOF

CROSS REFERENCE TO RELATED APPLICATIONS

This patent application is a 35 U.S.C. § 371 US national stage of International Patent Application PCT/EP2015/079298, filed Dec. 10, 2015, claiming the benefit of EP Patent Application No. 14384202.9, filed Dec. 10, 2014, both of which are incorporated here by reference in their entireties.

SEQUENCE LISTING STATEMENT

A sequence listing containing the file named 48638-166922.TXT which is 4259 bytes (measured in MS-Windows®) and created on Jun. 7, 2017, comprises 14 sequences, is provided herewith via the USPTO's EFS system, and is incorporated herein by reference in its entirety.

FIELD OF THE INVENTION

The invention relates to the field of probiotic strains, more particularly to the field of probiotic strains having cholesterol absorbing capacity and therapeutic uses thereof. The invention also relates to the treatment of dyslipidemias using probiotic strains.

BACKGROUND

Hypercholesterolemia is the most important risk factor for cardiovascular diseases and is considered one of the major causes of death and disability in many countries. It has been shown that a 1% reduction in serum cholesterol concentration may reduce the risk of coronary heart disease by 2-3%. Drug therapy for hypercholesterolemia has undesirable side effects that have raised concerns about their therapeutic use. Hence, a more natural method of decreasing serum cholesterol concentration in humans is required.

Lactobacilli and other lactic acid-producing bacteria play important roles in balancing digestive functions and helping with cholesterol removal, although research has not yet established a dose-effect relationship. Because of their ability to deconjugate bile salts, in recent years there has been interest in the possibility of using lactic acid bacteria as biological hypocholesterolemic agents. Several studies have proposed a relationship between consumption of lactic acid bacteria and reduction of cholesterol concentrations in blood of humans, rats and chickens. The presence of bile salt hydrolase (BSH) has a selective advantage for this bacterium in bile salt rich environments. BSH activity benefits the bacterium by enhancing its resistance to conjugated bile salts and increasing its survival in the gastrointestinal tract and thus its ability to colonize it. Studies on deconjugation of bile salts and cholesterol-reducing ability of lactobacilli have mostly been carried out on strains isolated from humans, swine and fermented milk preparations.

Strains of *Lactobacillus acidophilus* and bifidobacteria have been reported to assimilate cholesterol from laboratory media. Thus, both types of bacteria may have the potential to reduce serum cholesterol in humans. Many attempts have been made to elucidate the mechanism involved in the hypocholesterolemic action of lactic acid bacterial strains. One proposed mechanism is reduction of cholesterol by the cell wall during growth. Another possible mechanism is deconjugation of bile salts by bacteria producing BSH. However, these mechanisms require that the bacteria are alive to successfully reduce serum cholesterol.

Thus, there is still a need in the art to provide probiotic-based therapies that are efficient for the treatment of dyslipidemias, particularly hypercholesterolemia.

BRIEF DESCRIPTION OF THE INVENTION

In a first aspect, the present invention relates to a probiotic strain selected from *Lactobacillus reuteri* V3401 with accession number CECT 8605 and *Bifidobacterium breve* BT820 with accession number CECT 8606, or a variant of said probiotic strain having cholesterol-absorbing capacity.

In another aspect, the present invention relates to a biologically pure culture comprising a probiotic strain according to the invention.

In another aspect, the present invention relates to a composition comprising a probiotic strain according to the invention.

In another aspect, the present invention relates to a pharmaceutical product comprising a probiotic strain according to the invention.

In another aspect, the present invention relates to a nutritional product comprising a probiotic strain according to the invention.

In another aspect, the present invention relates to a feed comprising a probiotic strain according to the invention.

In another aspect, the present invention relates to a cell membrane- or cell wall-enriched fraction of a probiotic strain according to the invention.

In another aspect, the present invention relates to a method to obtain a probiotic strain according to the invention with increased cholesterol-absorbing capacity comprising a step of inactivating the cells.

In another aspect, the present invention relates to a method to obtain a probiotic strain according to the invention with increased cholesterol-absorbing capacity comprising a step of culturing the cells at a pH between 6 and 9 during their exponential phase.

In another aspect, the present invention relates to a method to obtain a microorganism with increased cholesterol-absorbing capacity comprising contacting a microorganism having cholesterol-absorbing with a composition comprising a peptidoglycan hydrolase activity.

In another aspect, the present invention relates to a cell obtainable by any of the methods to obtain a microorganism with increased cholesterol-absorbing capacity according to the invention.

In another aspect, the present invention relates to a probiotic strain according to the invention for use as a medicament.

In another aspect, the present invention relates to a cell obtainable by any of the methods to obtain a microorganism with increased cholesterol-absorbing capacity according to the invention for use as a medicament.

In another aspect, the present invention relates to a probiotic strain according to the invention for use in the treatment and/or prevention of a disease or condition selected from the group consisting of dyslipidemia, insulin resistance and metabolic syndrome.

In another aspect, the present invention relates to a cell obtainable by any of the methods to obtain a microorganism with increased cholesterol-absorbing capacity according to the invention for use in the treatment and/or prevention of a disease or condition selected from the group consisting of dyslipidemia, insulin resistance and metabolic syndrome.

DETAILED DESCRIPTION OF THE INVENTION

Figure 1:
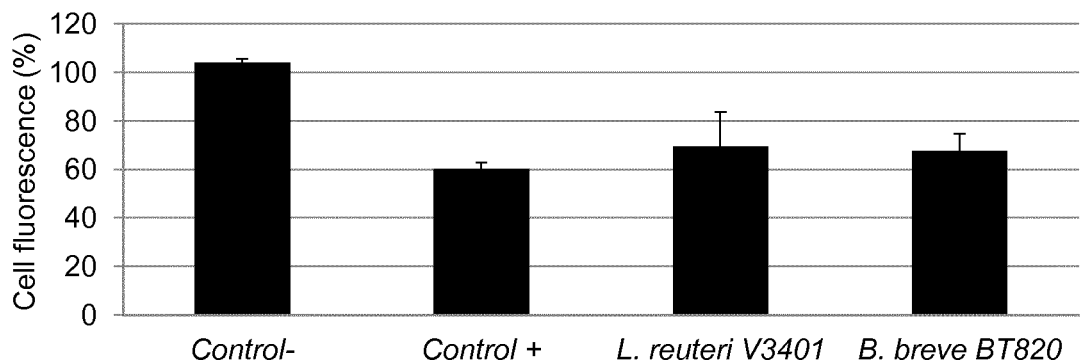
FIG. 1: Relative cell fluorescence average (%) of H-T29 enterocytes incubated with fluoresterol (control −) and with Ezetimibe (control +), L. reuteri V3401 or B. breve BT820 bacterial suspensions.

The authors of the present invention have identified two probiotic strains, Lactobacillus reuteri V3401 (accession number CECT 8605) and Bifidobacterium breve BT820 (accession number CECT 8606), that successfully reduce the absorption of fluoresterol, a fluorescent cholesterol analogue, and cholesterol by intestinal epithelial cells in in vitro and in vivo assays. The mechanism by which they exert their effect is based on their capacity to absorb cholesterol, thereby sequestering cholesterol from the intestinal tract and reducing the amount available to be absorbed by the intestinal epithelium. Furthermore, the authors of the invention have determined that the cholesterol-absorbing capacity of the strains can surprisingly be induced through an increase in a lytic activity that appears to be specific to the *L. reuteri* V3401 (CECT 8605) strain. This unexpected finding enables the activation of the cholesterol-absorbing function in microorganisms with said existing function.

Strains and Culture

In a first aspect, the invention relates to a probiotic strain selected from *Lactobacillus reuteri* V3401 with accession number CECT 8605 and *Bifidobacterium breve* BT820 with accession number CECT 8606, or a variant of said strain having cholesterol-absorbing capacity, hereinafter "the probiotic strain of the invention".

The term "strain", as used herein, refers to a genetic variant or subtype of a microorganism species, preferably a bacterial species. The term "probiotic strain", as used herein, refers to a live strain of a microorganism, preferably a bacterium, which, when administered in adequate amounts, confers a health benefit on the host. Hosts suitable in the context of the invention includes any mammal, preferably primates, such as human beings and chimpanzees, pigs, horses, cows, goats, ewes, dogs, cats, rats and mice; more preferably human beings. Other suitable hosts include birds, preferably chickens, ducks, geese, swans, pheasants, pigeons, doves, and ostriches.

The present invention contemplates a probiotic strain selected from:

*Lactobacillus reuteri* V3401 strain, deposited in the Colección Española de Cultivos Tipo (CECT) with accession number CECT 8605, or a variant thereof having cholesterol-absorbing capacity, and

*Bifidobacterium breve* BT820, deposited in the CECT with accession number CECT 8606, or a variant thereof having cholesterol-absorbing capacity.

Thus the invention also relates to variants of the *L. reuteri* V3401 strain and of the *B. breve* BT820 strain having cholesterol-absorbing capacity. As used herein, the term "variant" or "mutant" of a strain refers to any naturally-occurring or specifically developed strain obtained from the reference strain X, mainly by mutation, that maintains the cholesterol-absorbing capacity of the reference strain, i.e. of the CECT 8605 *L. reuteri* V3401 strain or of the CECT 8606 *B. breve* BT820 strain.

Variants may or may not have the same identifying biological characteristics of the specific strains exemplified herein, provided they share similar advantageous properties in terms of their cholesterol-absorbing capacity of the reference strain. For example, the 16S rRNA genes of a "variant" strain as contemplated herein may share about 85%, 86%, 87%, 88%, 89%, 90%, 91%, 92%, 93%, 94%, 95%, 96%, 97%, 98% or 99% sequence identity with a strain disclosed herein.

In another embodiment, a variant of the strains according to the present invention refer to any strain the genome of which hybridizes under stringent conditions with the genome of any of the CECT 8605 *L. reuteri* V3401 strain or of the CECT 8606 *B. breve* BT820 strain. In general, a low stringency hybridization reaction is carried out at about 40 degrees centigrade in 10×SSC or a solution of equivalent ionic strength/temperature. A moderate stringency hybridization is typically performed at about 50 degrees centigrade in 6×SSC, and a high stringency hybridization reaction is generally performed at about 60 degrees centigrade in 1×SSC.

In another embodiment, the degree of relatedness between the variant and the parent strains is determined as the average nucleotide identity (ANI), which detects the DNA conservation of the core genome (Konstantinidis K and Tiedje J M, 2005, Proc. Natl. Acad. Sci. USA 102: 2567-2592). In some embodiments, the ANI between the variant and the parent strain is of about 95%, about, 96%, about 97%, of about 98%, of about 99%, of about 99.1%, of about 99.5%, of about 99.6%, of about 99.7%, of about 99.8%, of about 99.9%, of about 99.99%, of about 99.999%, of about 99.9999%, of about 99.99999%, of about 99.999999% or more but less than 100%.

In another embodiment, the degree of relatedness between the variant and the parent strains is determined as the Tetranucleotide Signature Frequency Correlation Coefficient, which is based on oligonucleotide frequencies (Bohlin J. et al. 2008, BMC Genomics, 9:104). In some embodiments, the Tetranucleotide Signature Frequency Correlation coefficient between the variant and the parent strain is of about 0.99, 0.999, 0.9999, 0.99999, 0.999999, 0.999999 or more but less than 1.

In another embodiment, the degree of relatedness between the variant and the parent strains is determined as the degree of similarity obtained when analysing the genomes of the parent and of the variant strain by Pulsed-field gel electrophoresis (PFGE) using one or more restriction endonucleases. The degree of similarity obtained by PFGE can be measured by the Dice similarity coefficient. In some embodiments, the Dice similarity coefficient between the variant and the parent strain is of about 95%, about, 96%, about 97%, of about 98%, of about 99%, of about 99.1%, of about 99.5%, of about 99.6%, of about 99.7%, of about 99.8%, of about 99.9%, of about 99.99%, of about 99.999%, of about 99.9999%, of about 99.99999%, of about 99.999999% or more but less than 100%.

In another embodiment, a strain is considered a variant of a given parent strain when both strains have the same ribotype, as obtained using any of the methods known in the art an described, for instance, by Bouchet et al. (Clin. Microbiol. Rev., 2008, 21:262-273).

In another embodiment, the degree of relatedness between the variant and the parent strains is the Pearson correlation coefficient obtained by comparing the genetic profiles of both strains obtained by repetitive extragenic palindromic element-based PCR (REP-PCR) (see e.g. Chou and Wang, Int J Food Microbiol. 2006, 110:135-48). In some embodiments, the Pearson correlation coefficient obtained by comparing the REP-PCR profiles of the variant and the parent strain is of about 0.99, 0.999, 0.9999, 0.99999, 0.999999, 0.999999 or more but less than 1.

In another embodiment, the degree of relatedness between the variant and the parent strains is the linkage distance obtained by comparing the genetic profiles of both strains obtained by Multilocus sequence typing (MLST) (see e.g. Maiden, M. C., 1998, Proc. Natl. Acad. Sci. USA 95:3140-3145). In some embodiments, the linkage distance obtained by MLST of the variant and the parent strain is of about 0.99, 0.999, 0.9999, 0.99999, 0.999999, 0.999999 or more but less than 1.

In a preferred embodiment, the variant and the parent strain are of the same genus. In a still more preferred embodiment, the variant and the parent strain are of the same species or subspecies.

The term "cholesterol-absorbing capacity", as used herein, refers to the property by which a strain is able to capture cholesterol and incorporate it into its bacterial cell structure. The person skilled in the art will recognise that there are a number of technologies in the art suitable for determining the cholesterol-absorbing capacity of a cell. This includes, without limitation, the method described in the Examples section of the present patent application, which are based on the detection by fluorometry or fluorocytometry of the incorporation of fluoresterol or NBD-cholesterol, which is a cholesterol analogue of formula (I), from micelles into the bacteria.

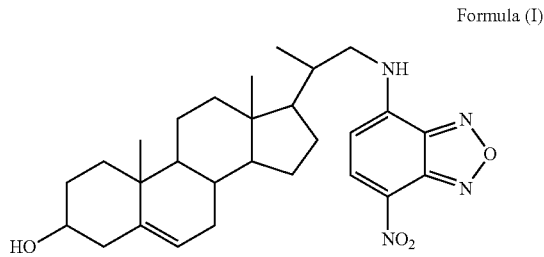 [SMILES: CC(CNc1ccc([N+](=O)[O-])c2nonc12)C1CCC2C3CC=C4CC(O)CCC4(C)C3CCC12C]

Formula (I)

Variants suitable for use in the present invention include those variants having at least 40%, at least 50%, at least 60%, at least 70%, at least 80%, at least 90%, at least 95%, at least 96%, at least 97%, at least 98%, at least 99%, at least 100%, at least 110%, at least 120%, at least 130%, at least 140%, at least 150% or more cholesterol-absorbing capacity with respect to the cholesterol-absorbing capacity of the strain from which they derive.

In a particular embodiment, the probiotic strain of the invention is in the form of viable cells. In another particular embodiment, the probiotic strain of the invention is in the form of non-viable cells. The term "viability", as used herein, refers to the ability of a cell to maintain itself or recover its potentialities and survive until they are able to divide. Thus, a cell that is viable indicates that the cell is able to survive and divide; conversely, a cell that is non-viable indicates that the cell is not able to survive and divide. It will be appreciated that non-viable cells include dead cells.

Viability can be determined by a number of assays that are conventional in the art. These include cytolysis or membrane leakage assays, such as the lactate dehydrogenase assay, the propidium iodide assay, the trypan blue assay and the 7-aminoactinomycin D assay, as well as genomic and proteomic assays that test the activation of stress pathways using DNA microarrays and protein chips.

The probiotic strain of the invention has a viability of 0%, or at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%. The percentage of cell viability reflects the percentage of cells that are able to maintain themselves or recover their potentialities and survive until they are able to divide. Conversely, the probiotic strain of the invention has a non-viability of 100%, or at least 95%, or at least 90%, or at least 85%, or at least 80%, or at least 75%, or at least 70%, or at least 65%, or at least 60%, or at least 55%, or at least 50%, or at least 45%, or at least 40%, or at least 35%, or at least 30%, or at least 25%, or at least 20%, or at least 15%, or at least 10%, or at least 5%, or 0%. The percentage of cell non-viability reflects the percentage of cells that are not able to maintain themselves or recover their potentialities and survive until they are able to divide.

In another aspect, the invention relates to a biologically pure culture of the probiotic strain of the invention.

The term "biologically pure culture", as used herein, refers to a culture in which the bacteria of the invention is found in a ratio of 90% or over, for example 95% or over, 96% or over, 97% or over, 98% or over, 99% or over or 100%, compared to other organisms present in the culture. The term "culture", as used herein, refers to a population of the bacteria of the invention. A culture may comprise other elements than the bacteria of the invention, such as the culture medium or any other substance that could be added to the culture medium beneficial for the culture growth or maintenance. The term "culture medium" or "medium" is recognized in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. Similarly, a powder mixture that when mixed with water or other liquid becomes suitable for cell culture may be termed a "powdered medium". "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. Any conventional culture medium appropriate for lactic acid bacteria or bifidobacteria culture known in the art can be used in the present invention, such as, for instance, MRS medium, HANK'S medium, APT medium, RCM medium, LM17 medium, BSM medium and Elliker medium.

In another aspect, the invention relates to a cell membrane- or cell wall-enriched fraction of a probiotic strain of the invention.

The term "cell membrane-enriched fraction", as used herein, refers to the preparation resulting from cell fractionation procedures that contains a content of cell membrane higher than that in unfractionated cells. Similarly, the term "cell wall-enriched fraction", as used herein, refers to the preparation resulting from cell fractionation procedures that contains a content of cell wall higher than that in unfractionated cells. Techniques to obtain cell membrane-enriched fractions and cell wall-enriched fractions are well-known and conventional in the art, and include a combination of homogenisation, such as osmotic homogenisation or physical homogenisation using mortars, pestles, blenders or ultrasounds, and fractionation techniques, such as centrifugation.

Methods to Increase the Cholesterol-Absorbing Capacity of Microorganisms

The authors of the present invention have also determined that, unexpectedly, the capacity to absorb cholesterol of the CECT 8605 *L. reuteri* V3401 strain and the CECT 8606 *B. breve* BT820 strain can be induced or incremented by subjecting the cells to cell inactivation (Example 3). Alternatively, the same effect was observed when the cells are grown at a pH of 6 or higher (Example 4).

Thus, in another aspect, the invention relates to a method to obtain a probiotic strain selected from *L. reuteri* V3401 with accession number CECT 8605 and *B. breve* BT820 with accession number CECT 8606, or a variant of said strain having cholesterol-absorbing capacity, with increased cholesterol-absorbing capacity, Hereinafter "the first method of the invention", comprising a step of inactivating the cells or a step of culturing the cells at a pH of 6 or higher.

The terms "cholesterol-absorbing capacity", "probiotic strain", "*L. reuteri* V3401 with accession number CECT 8605", "*B. breve* BT820 with accession number CECT 8606", and "variant" have been described in detail in the context of the probiotic strain of the invention, and their definitions and embodiments are included here by reference.

The first method of the invention comprises a step of inactivating the cells. It will be apparent for the person skilled in the art that this step may be performed on a culture of the probiotic strain of the invention or on isolated cells. The term "cell inactivation", as used herein, refers to a process of transforming a cell from viable to non-viable. There are different methods to determine if a cell is viable or non-viable, which have been described in the context of the strain of the invention. The resulting cells consist of 0% viable cells and 100% non-viable cells, or at least 1% viable cells and 99% non-viable cells, or at least 5% viable cells and 95% non-viable cells, or at least 10% viable cells and 90% non-viable cells, or at least 15% viable cells and 85% non-viable cells, or at least 20% viable cells and 80% non-viable cells, or at least 25% viable cells and 75% non-viable cells, or at least 30% viable cells and 70% non-viable cells, or at least 35% viable cells and 65% non-viable cells, or at least 40% viable cells and 60% non-viable cells, or at least 45% viable cells and 55% non-viable cells, or at least 50% viable cells and 50% non-viable cells, or at least 55% viable cells and 45% non-viable cells, or at least 60% viable cells and 40% non-viable cells, or at least 65% viable cells and 35% non-viable cells, or at least 70% viable cells and 30% non-viable cells, or at least 75% viable cells and 25% non-viable cells, or at least 80% viable cells and 20% non-viable cells, or at least 85% viable cells and 15% non-viable cells, or at least 90% viable cells and 10% non-viable cells, or at least 95% viable cells and 5% non-viable cells, or at least 99% viable cells and 1% non-viable cells, There are different methods of inactivating cells that are available in the art, including thermal inactivation, microwave inactivation, pressure inactivation, acid inactivation, base inactivation, alcohol inactivation and peroxide inactivation.

In a particular embodiment of the first method of the invention, the inactivation is selected from the group consisting of thermal inactivation, microwave inactivation, pressure inactivation, acid inactivation, base inactivation, alcohol inactivation and peroxide inactivation.

The term "thermal inactivation", as used herein, refers to the inactivation of cells using high temperatures. Usually, this is achieved by increasing the temperature of the cells or the medium containing them to over 50° C. Methods suitable for thermal inactivation are well-known in the art and include, without limitation, the method described in the Examples section, which consists of incubating a culture containing the probiotic strain of the invention at 120° C. for 20 min and allowing the culture to cool to room temperature.

The term "microwave inactivation", as used herein, refers to the inactivation of cells using microwaves. Methods suitable for microwave inactivation are well-known in the art and include, without limitation, subjecting the cells or the medium containing them containing the probiotic strain of the invention to microwaves using a laboratory microwave apparatus. For example, inactivation may be achieved by gradually increasing for 3 min the power of the apparatus up to 300 W, and maintaining these conditions for a further 5 min.

The term "pressure inactivation", as used herein, refers to the inactivation of cells using pressure. Methods suitable for pressure inactivation are well-known in the art and include, without limitation, homogenisation, for example using a homogenizer or a French press. For example, cell inactivation may be achieved using a high pressure homogenizer at a pressure of 1,500-2,000 bar and 15-20 pulses/min for 10 min.

The term "acid inactivation", as used herein, refers to the inactivation of cells by lowering the pH. This is normally achieved by adding an acid to the cells or the medium containing them and subsequently neutralizing the cells or the medium. Strong acids are preferred for the purposes of inactivating cells, and include, without limitation, hydrochloric acid (HCl), hydroiodic acid (HI), hydrobromic acid (HBr), perchloric acid ($HClO_4$), nitric acid ($HNO_3$), and sulfuric acid ($H_2SO_4$). The strength of an acid refers to its ability or tendency to lose a proton. For example, inactivation may be achieved by adding $H_2SO_4$ to the cells until a concentration of 80 mM is reached, incubating the cells at 55° C. for 4 h, and neutralising by adding 10 M NaOH until the pH is 7.

Analogously, the term "base inactivation", as used herein, refers to the inactivation of cells using increasing the pH. This is normally achieved by adding a base to the cells or the medium containing them and subsequently neutralizing the cells or the medium. Strong bases are preferred for the purposes of inactivating cells, and include, without limitation, potassium hydroxide (KOH), barium hydroxide [$Ba(OH)_2$], cesium hydroxide (CsOH), sodium hydroxide (NaOH), strontium hydroxide [$Sr(OH)_2$], calcium hydroxide [$Ca(OH)_2$], lithium hydroxide (LiOH), and rubidium hydroxide (RbOH). The strength of a base refers to its ability to deprotonate an acid. For example, inactivation may be achieved by adding NaOH to the cells until a concentration of 80 mM is reached, incubating the cells at 55° C. for 4 h, and neutralising by adding 96% $H_2SO_4$ until the pH is 7.

The term "peroxide inactivation", as used herein, refers to the inactivation of cells using peroxide. A peroxide is a compound containing an oxygen-oxygen single bond or the peroxide anion, $O_2^{2-}$, and includes hydrogen peroxide ($H_2O_2$), Superoxides, dioxygenyls, ozones and ozonides. For example, cell inactivation may be achieved by incubating the cells in 1.5% (v/v) $H_2O_2$ at 37° C. for 1 h. Subsequently, the $H_2O_2$ is eliminated by treating the cells with catalase.

The term "alcohol inactivation", as used herein, refers to the inactivation of cells using alcohol. An alcohol is an organic hydroxyl compound with the ⁻OH functional group bound to a saturated carbon atom, and includes ethanol, methanol, isopropanol, butanol. For example, cell inactivation may be achieved by making a 1:1 dilution of the cell culture with 96% ethanol, and incubating at 37° C. for 1 h. Subsequently, the ethanol is eliminated by evaporation in a rotary evaporator or rotavap.

In a preferred embodiment, the inactivation is thermal inactivation.

As a result from the inactivating step, the cells of the probiotic strain of the invention become non-viable, or even dead.

Alternatively, the first method of the invention comprises a step of culturing the cells at a pH between 6 and 9 during their active growth phase.

In order to grow the cells according to this alternative of the first method of the invention, it is necessary that the culture medium has a pH between 6 and 9, preferably between 6 and 8.5, more preferably between 6 and 8, even more preferably between 6 and 7.5, even more preferably between 6 and 7, or even more preferably between 6 and 6.5. In a particular embodiment, the pH is 6.

The person skilled in the art, using the common general knowledge, will immediately understand that a pH between 6 and 9 may be obtained by using a medium with that pH. Media with a pH within this range are well known in the art, but a pH between 6 and 9 may also be obtained in any medium by adjusting the pH with a suitable acid, such as HCL, or base, such as NaOH.

In another particular embodiment, the first method of the invention comprises a step of culturing the cells at a pH of 6 to 9, and it further comprises a step of inactivating said cells.

The term "active growth phase", as used herein, refers to the stage of bacterial growth characterized by an increase in total biomass or in cell numbers. Bacterial growth may be expressed in the form of a growth curve, which usually plots the log of the number of cells against time. The growth of bacteria in batch culture can be modeled with four different phases:

Lag phase, during which bacteria adapt to growth conditions and and the rate of increase in cell numbers is minimal.

Log phase or exponential phase, characterised by a growth rate which gradually increases (early log/exponential phase) until it is both constant and maximal for the particular growth conditions.

Stationary phase, characterised by a growth rate which declines (early stationary phase) and eventually reaches zero.

Death phase, during which the number of viable cells in the culture declines.

Thus, the person skilled in the art will immediately realise that the active growth phase expands from the early log/exponential phase until the early stationary phase.

Bacterial growth may be measured by monitoring cell numbers, by measuring the increase in dry weight of biomass formed in a given time interval, by monitoring the uptake and metabolism (or release) of particular substances, and by measuring the amount of a radioactive metabolite incorporated in biomass in a given time. Typically, cell numbers are measured by determining the concentration of bacteria in a suspension by measuring the optical density in a spectrophotometer; OD600 is generally used for this purpose.

The cells resulting from the first method of the invention present a cholesterol-absorbing capacity that is increased compared to the cells that have not undergone inactivation.

The term "increased cholesterol-absorbing capacity", as used herein, refers to a capacity to absorb cholesterol that is at least 101%, at least 105%, at least 110%, at least 120%, at least 130%, at least 140%, at least 150%, at least 160%, at least 170%, at least 180%, at least 190%, at least 200%, at least 250%, at least 300%, at least 500%, at least 1000% or more of that shown by a cell that has not been subjected to inactivation. Methods suitable to determine the cholesterol-absorbing capacity of a cell include the method described in the Examples section of the present patent application, which are based on the detection by fluorometry or fluorocytometry of the incorporation of fluoresterol from micelles into the bacteria.

The invention also contemplates the cell obtained by the first method of the invention.

Thus, in another aspect, the invention relates to a cell obtainable by a method to increase the cholesterol-absorbing capacity of a probiotic strain selected from L. reuteri V3401 with accession number CECT 8605 and B. breve BT820 with accession number CECT 8606, or a variant of said strain having cholesterol-absorbing capacity, comprising a step of inactivating the cells.

In another aspect, the invention relates to a cell obtainable by a method to increase the cholesterol-absorbing capacity of a probiotic strain selected from L. reuteri V3401 with accession number CECT 8605 and B. breve BT820 with accession number CECT 8606, or a variant of said strain having cholesterol-absorbing capacity, comprising a step of culturing the cells at a pH of 6 or higher.

Surprisingly, the authors of the invention have also observed that cells with an existing capacity to absorb cholesterol can be modified in order to increase their cholesterol absorption ability. Said modification is carried out by incubating the cells with a cell extract obtained from the CECT 8605 L. reuteri V3401 strain, as shown in Example 7. The agent causing this increase in absorption of cholesterol-absorbing activity was identified to be an enzyme with murein hydrolase activity. Without wishing to be bound by any theory, the peptidoglycan hydrolase is suspected to play a role in permeabilising the cell wall of the microorganism having cholesterol-absorbing capacity, or in increasing the affinity of its cell wall for cholesterol-containing micelles. This would result in an increased amount of cholesterol being absorbed by the microorganism. Moreover, this effect appears to be specific to a peptidoglycan hydrolase expressed by CECT 8605 L. reuteri V3401 strain.

Thus, in another aspect, the invention relates to a method to obtain a microorganism with increased cholesterol-absorbing capacity, hereinafter "the second method of the invention", comprising contacting a microorganism having cholesterol-absorbing capacity with a composition comprising an enzyme with peptidoglycan hydrolase activity.

The terms "cholesterol-absorbing capacity" and "increased cholesterol-absorbing capacity" have been described in detail in the context of the probiotic strain of the invention and the first method of the invention, and their definitions and embodiments are included here by reference.

The second method of the invention comprises a step of contacting a microorganism having cholesterol-absorbing capacity with a composition comprising a peptidoglycan hydrolase.

The term "microorganism", as used herein, refers to a microscopic organism, which may be a single cell or multicellular organism, and may also be prokaryotic or eukaryotic organisms with cholesterol-absorbing capacity. Methods to determine if a microorganism possesses a capacity to absorb cholesterol have been described in detail in the context of the probiotic strain of the invention and are included here by reference.

In particular embodiment, the microorganism having cholesterol-absorbing capacity is prokaryotic. In another particular embodiment, the microorganism having cholesterol-absorbing capacity is eukaryotic.

In a preferred embodiment, the microorganism having cholesterol-absorbing capacity is a bacterium of the CECT 8605 L. reuteri V3401 strain. In another preferred embodiment, the microorganism having cholesterol-absorbing capacity is a bacterium of the CECT 8606 of the *B. breve* BT820 strain.

For the purposes of the invention, the composition contacting a microorganism having cholesterol-absorbing capacity comprises a peptidoglycan hydrolase. The term "peptidoglycan hydrolase" or "murein hydrolase", as used herein, refers to an enzyme that catalyses the hydrolysis of peptidoglycans, i.e. an enzyme capable of cleaving covalent bonds in peptidoglycan sacculi or its fragments. The physiological functions of these enzymes include the regulation of cell wall growth, the separation of daughter cells during cell division and autolysis, and the turnover of peptidoglycan during growth, where turnover products serve as signaling molecules for recognition of bacteria by other organisms and, in some bacteria, for the induction of β-lactamase. Specialized hydrolases enlarge the pores in the peptidoglycan for the assembly of large trans-envelope complexes (pili, flagella, secretion systems), or they specifically cleave peptidoglycan during sporulation or spore germination. Moreover, peptidoglycan hydrolases are involved in lysis phenomena such as fratricide or developmental lysis occurring in bacterial populations.

The peptidoglycan hydrolase activity refers to the hydrolysis of amide, peptide and glycosidic bonds in peptidoglycan. The different peptidoglycan hydrolases as well as their respective cleavage sites are described in Vollmer et al., 2008 (Vollmer et al., 2008, FEMS Microbiol Rev 32:259-86). Briefly, peptidoglycan hydrolases include the following:

N-Acetylmuramyl-L-alanine amidases, which hydrolyse the amide bond between MurNAc and the N-terminal L-alanine residue of the stem peptide. These include some amidases (anhAmi) specifically cleave at 1,6-anhydroMurNAc residues.

Carboxypeptidases which hydrolyse peptide bonds to remove C-terminal D- or L-amino acids. These include DD-carboxypeptidase, LD-carboxypeptidase, and DL-carboxypeptidase.

Endopeptidases, which cleave amide bonds in the peptides. These include DD-endopeptidase, LD-endopeptidase, and DL-endopeptidase.

Glycosidases, which cleave glycan strands. There are three types of glycosidases:
a) N-acetylglucosaminidases, which hydrolyse the glycosidic bond between N-acetyl-β-D-glucosamine residues and adjacent monosaccharides,
b) lysozymes, and
c) lytic transglycosylases, Lysozymes and lytic transglycosylases are also collectively known as N-acetyl-β-D-muramidases (muramidases) and cleave the same glycosidic bond, i.e. the (β1,4-glycosidic bond between MurNAc and GlcNAc residues in peptidoglycan (FIG. 1B).

The activity of a peptidoglycan hydrolase is often specific for a certain peptidoglycan type, for the presence or the absence of secondary modifications, or for either high-molecular weight peptidoglycan or small fragments. Thus, the peptidoglycan hydrolase is selected from the group consisting of an N-Acetylmuramyl-L-alanine amidase, a carboxypeptidase, an endopeptidase, or a glycosidase.

In a particular embodiment, the peptidoglycan hydrolase is an N-Acetylmuramyl-L-alanine amidase. In another particular embodiment, the peptidoglycan hydrolase is a carboxypeptidase. In another particular embodiment, the peptidoglycan hydrolase is an endopeptidase. In another particular embodiment, the peptidoglycan hydrolase is a glycosidase selected from the group consisting of an N-acetylglucosaminidase, a lysozyme and a lytic transglycosylase.

In a preferred embodiment, the glycosidase is an N-acetylglucosaminidase. In another preferred embodiment, the glycosidase is a lysozyme. In another preferred embodiment, the glycosidase is a lytic transglycosylase.

In another particular embodiment, the peptidoglycan hydrolase is a peptidoglycan hydrolase specific of the CECT 8605 *L. reuteri* V3401 strain.

For the peptidoglycan hydrolase to exert its effect in increasing the capacity to absorb cholesterol in a microorganism having cholesterol-absorbing capacity, the peptidoglycan hydrolase needs to be put in contact with said organism. The person skilled in the art will easily understand that the contacting step may be carried out in diverse ways. One of such ways is by recombinantly expressing the peptidoglycan hydrolase in said organism.

Thus, in a particular embodiment the composition comprising a peptidoglycan hydrolase is an extract of an organism which expresses said peptidoglycan hydrolase.

The recombinant expression of the peptidoglycan hydrolase may be performed using methods that are conventional in the art. Preferably, the nucleotide sequence encoding the peptidoglycan hydrolase also encodes any naturally occurring signal peptide that the enzyme may contain. For example, the nucleotide sequence may be operatively bound to expression-regulating sequences, thereby forming a gene construct or expression cassette. As used herein, the term "operably linked" means that the peptidoglycan hydrolase encoded by the nucleotide sequence is expressed in the correct reading frame under the control of the control sequence or the expression-regulating sequence. The expression cassette of the invention can be obtained by molecular biology techniques that are well known in the art. Control sequences are sequences that control and regulate transcription and, where applicable, the translation of said peptidoglycan hydrolase, and include promoter sequences, sequences encoding transcriptional regulators, ribosome binding sequences (RBS) and/or transcription terminator sequences. Promoters suitable in the context of the invention include, without limitation, inducible and constitutive promoters. The expression cassette may further include an enhancer, which can be adjacent or distant to the promoter sequence and can function by increasing the transcription. In a particular embodiment, said expression control sequence is functional in prokaryotic cells. In another particular embodiment, said expression control sequence is functional in eukaryotic cells.

Advantageously, the expression cassette further comprises a marker or gene encoding a motif or phenotype which allows selecting the host cell transformed with said expression cassette. Illustrative examples of said markers that could be present in the expression cassette of the invention include antibiotic resistance genes, genes resistant to toxic compounds, and, in general, all those that allow selecting the genetically transformed cells.

The expression cassette may be inserted into an appropriate vector. The choice of vector will depend on the host cell in which it will be subsequently introduced, i.e. on the microorganism having cholesterol-absorbing capacity. For illustrative purposes, the vector wherein said nucleic acid sequence is introduced can be a plasmid or a vector which, when introduced into a host cell, is integrated or not in the genome of said cell. Obtaining said expression vector may be performed by conventional methods known to those skilled in the art. In a particular embodiment, said recombinant vector is a useful vector to transform prokaryotic cells. In a particular embodiment, said recombinant vector is a useful vector to transform eukaryotic cells.

The vector comprising the sequence encoding the peptidoglycan hydrolase can be used to transform, transfect or infect cells of the microorganism having cholesterol-absorbing capacity. Transformed, transfected or infected cells can be obtained by methods conventional known to those skilled in the art. Such cells can be prokaryotic or eukaryotic. Hence, the resulting transformed, transfected or infected cell comprises the sequence encoding the peptidoglycan hydrolase.

The gene construct, expression cassette and vector containing the sequence encoding the peptidoglycan hydrolase are also aspects of the present invention.

Once the microorganism having cholesterol-absorbing capacity contains the expression vector comprising the peptidoglycan hydrolase, said peptidoglycan hydrolase may be recombinantly expressed by methods conventional known to the person skilled in the art. For example, the recombinant expression of the peptidoglycan hydrolase may be inducible or constitutive. Preferably, the recombinantly-expressed peptidoglycan hydrolase is secreted.

Thus, the resulting recombinantly-expressed peptidoglycan hydrolase is forming part of a composition, preferably extracellular that is in contact with the microorganism having cholesterol-absorbing capacity, thereby exerting its function in increasing said cholesterol-absorbing capacity.

Since the peptidoglycan hydrolase responsible for incrementing the capacity to absorb cholesterol of a microorganism having cholesterol-absorbing capacity appears to be specifically expressed in the CECT 8605 *L. reuteri* V3401 strain, the second method of the invention may also be carried out by applying a protein extract obtained from said strain.

Thus, in another particular embodiment, the composition comprising a peptidoglycan hydrolase is a protein extract of the CECT 8605 *L. reuteri* V3401 strain. Preferably, the CECT 8605 *L. reuteri* V3401 strain cells are cultured at a pH of 6 or higher.

The term "protein extract", as used herein, refers to the protein content of a cell. In some embodiments, the protein extract refers to a "total protein extract" or "crude protein extract", which refers to the collection of proteins originated from the strains according to the present invention and almost no fragments or debris of cell walls and large organelles. According to one exemplary embodiment, the total tissue protein extract may be obtained by adding bacteria to a lysis buffer, but the present invention is not limited thereto. However, the total protein extract may be extracted using any extraction method known in the art.

Methods to obtain a protein extract are conventional and well known by the skilled person. Normally, proteins are brought into solution by breaking the cells containing them. There are several methods to achieve this, such as repeated freezing and thawing, sonication, homogenization by high pressure, filtration, or permeabilisation by organic solvents.

In some embodiments, the protein extract is at least partially fractionated in order to enrich in the peptidoglycan hydrolase activity, thereby obtaining a "peptidoglycan hydrolase-enriched extract". Any suitable method known in the art can be used to obtain the peptidoglycan hydrolase-enriched extract, such as affinity chromatography, ion exchange chromatography, filter, ultrafiltration, gel filtration, electrophoresis, salt precipitation, and dialysis etc. are appropriately selected and combined to enable separation and purification of the peptide. The degree of enrichment in peptidoglycan hydrolase activity can be determined by measuring the specific peptidoglycan hydrolase activity in the enriched extract (i.e. units of peptidoglycan hydrolase activity per mg of protein), wherein an increase with respect to the activity in the crude extract is indicative that the extract has been enriched in peptidoglycan hydrolase activity. In a preferred embodiment, the peptidoglycan hydrolase-enriched extract contains a peptidoglycan hydrolase activity which is at least 5%, at least 10%, at least 20%, at least 30%, at least 40%, at least 50%, at least 60%, at least 70%, at least 80%, at least 90% or at least 100% of the activity found in the crude extract. In another embodiment, the peptidoglycan hydrolase-enriched extract contains a peptidoglycan hydrolase activity which is at least 2-fold, 3-fold, 4-fold, 5-fold, 6-fold, 7-fold, 8-fold, 9.fold, 10-fold, 100-fold, 1000-fold, 10000-fold or more with respect to the activity in the crude extract.

The contacting step of the second method of the invention requires that the composition containing the peptidoglycan hydrolase contacts the microorganism having cholesterol-absorbing capacity for an amount of time sufficient to allow the peptidoglycan to be cleaved. The contacting step is of at least 1 s, at least 10 s, at least 30 s, at least 1 min, at least 5 min, at least 10 min, at least 30 min, at least 1 h, at least 2 h, at least 4 h, at least 6 h, at least 8 h, at least 10 h, at least 12 h, at least 24 h, or longer.

In order to determine whether microorganism has had its cholesterol-absorbing capacity increased, the person skilled in the art will recognise that the cholesterol-absorbing capacity needs to be determined and compared to the cholesterol-absorbing capacity of the same microorganism that has not been subjected to the second method of the invention. Methods to determine the cholesterol-absorbing capacity of a cell have been described in the context of the probiotic strain of the invention, and are included here by reference.

The invention also contemplates the cell obtained by the second method of the invention.

Thus, a cell obtainable by a method to increase the cholesterol-absorbing capacity of a microorganism having cholesterol-absorbing capacity, comprising contacting said microorganism with composition comprising a peptidoglycan hydrolase is another aspect of the present invention.

Compositions and Feeds or Nutritional Products

The person skilled in the art will immediately appreciate that the probiotic strain of the invention is particularly useful as part of a composition, a feed or a nutritional product.

Thus, in another aspect, the invention relates to a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

The terms "probiotic strain", "*L. reuteri* V3401 with accession number CECT 8605", "*B. breve* BT820 with accession number CECT 8606", "variant", and "cholesterol-absorbing capacity", have been described in detail in the context of the probiotic strain of the invention, and their definitions and embodiments are included here by reference.

In a particular embodiment, the composition comprises a mixture of probiotic strains of the invention.

Preferably, the composition comprises at least 2, at least 3, at least 4, or more of the strains of the invention, and wherein each of the strains is represented in the composition in a proportion from 0.1% to 99.9%, preferably from 1% to 99%, more preferably from 10% to 90%. In another embodiment, the composition comprises any of the bacterial strains of the invention together with another strain or mixture of strains and where each of the strains is represented in the composition in a proportion from 0.1% to 99.9%, preferably from 1% to 99%, more preferably from 10% to 90%. In another embodiment, the invention provides a composition which comprises a supernatant of a culture of one or more of the strains according to the invention. Preferably, the supernatant is represented in the composition in a proportion from 0.1% to 99.9%, more preferably from 1% to 99% and even more preferably from 10% to 90%.

In another particular embodiment, the invention also refers to compositions of the strains of this invention in a lyophilized, freeze-dried or dried form, which can be obtained by any conventional method known in the art.

In another particular embodiment, the probiotic strain or the mixture thereof is in the form of non-viable cells.

In another aspect, the invention relates to a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

The terms "probiotic strain", "*L. reuteri* V3401 with accession number CECT 8605", "*B. breve* BT820 with accession number CECT 8606", "variant", and "cholesterol-absorbing capacity", have been described in detail in the context of the probiotic strain of the invention, and their definitions and embodiments are included here by reference.

In a particular embodiment, the feed or nutritional product comprises a mixture of probiotic strains of the invention.

Preferably, the feed or nutritional product comprises at least 2, at least 3, at least 4, or more of the strains of the invention, and wherein each of the strains is represented in the composition in a proportion from 0.1% to 99.9%, preferably from 1% to 99%, more preferably from 10% to 90%. In another embodiment, the feed or nutritional product comprises any of the bacterial strains of the invention together with another strain or mixture of strains and where each of the strains is represented in the composition in a proportion from 0.1% to 99.9%, preferably from 1% to 99%, more preferably from 10% to 90%. In another embodiment, the invention provides a feed or nutritional product which comprises a supernatant of a culture of one or more of the strains according to the invention. Preferably, the supernatant is represented in the feed or nutritional product in a proportion from 0.1% to 99.9%, more preferably from 1% to 99% and even more preferably from 10% to 90%.

Non-limiting examples of suitable foodstuffs which can be used in the present invention are milk, yoghourt, cheese, curd, fermented milks, milk based fermented products, fermented cereal based products, fermented meat products, other milk based or cereal based powders, clinical nutrition formula, ice-creams, juices, bread, cakes or candies, animal feed formulations, semi- or synthetic diet formulations, infant formulae, clinical nutrition formulae, ice-creams, juices, flours, bread, cakes, candies or chewing-gums.

In another embodiment, the feed or nutritional product comprising a probiotic strain of the invention is in a lyophilized, freeze-dried or dried form, which can be obtained by any conventional method known in the art.

In another embodiment of the feed or nutritional product, the probiotic strain or the mixture thereof is in the form of non-viable cells.

Therapeutic Uses

The inventors have shown that the probiotic strains of the invention are able to reduce the absorption of fluoresterol of HT-29 cells, an enterocyte cell line, when co-cultured in the presence of fluoresterol-containing micelles, as shown in Example 1. This was a result of the probiotic cells competing with the HT-29 cells for capturing the micelles (see Example 2). This effect may be exploited in the treatment of diseases the level of cholesterol in plasma plays a role, such as in dyslipidemias. The inventors have demonstrated that the intake of the probiotic strains of the invention reduces total plasmatic cholesterol, the LDL/HDL index, and the level of glucemia in an in vivo model of hypercholesterolemia (see Example 8).

Thus, in another aspect, the invention relates to a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use as a medicament.

In another aspect, the invention relates to a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use in the treatment and/or prevention of a dyslipidemia.

Alternatively, this aspect may be reformulated to a use of a probiotic strain selected from *Lactobacillus reuteri* V3401 with accession number CECT 8605 and *Bifidobacterium breve* BT820 with accession number CECT 8606, or a variant of said strain having cholesterol-absorbing capacity for the manufacture of a medicament for the treatment and/or prevention of a dyslipidemia. Alternatively, this aspect may be reformulated to a method for the treatment and/or prevention of a dyslipidemia in a subject in need thereof, comprising administering a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

The terms "probiotic strain", "*L. reuteri* V3401 with accession number CECT 8605", "*B. breve* BT820 with accession number CECT 8606", "variant", and "cholesterol-absorbing capacity", have been described in detail in the context of the probiotic strain of the invention, and their definitions and embodiments are included here by reference.

The term "treatment" or "therapy", as used herein, includes any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment. Particularly, the term treatment relates to the administration of a probiotic strain selected from *Lactobacillus reuteri* V3401 with accession number CECT 8605 and *Bifidobacterium breve* BT820 with accession number CECT 8606, or a variant of said strain having cholesterol-absorbing capacity to a subject who has been diagnosed with a dyslipidemia.

The term "prevention", "preventing" or "prevent", as used herein, relates to the administration of a probiotic strain selected from *Lactobacillus reuteri* V3401 with accession number CECT 8605 and *Bifidobacterium breve* BT820 with accession number CECT 8606, or a variant of said strain having cholesterol-absorbing capacity to a subject who has not been diagnosed with a dyslipidemia, but who would normally be expected to develop said disease or be at increased risk for said disease. The prevention intends to avoid the appearance of the dyslipidemia. The prevention may be complete (e.g. the total absence of a disease). The prevention may also be partial, such that for example the occurrence of a disease in a subject is less than that which would have occurred without the administration of the inhibitor of the present invention. Prevention also refers to reduced susceptibility to a clinical condition.

The term "subject", as used herein, refers to all animals classified as mammals and birds and includes, but is not restricted to, domestic and farm animals, primates and humans, e.g., human beings, non-human primates, cows, horses, pigs, sheep, goats, dogs, cats, rodents, chickens, ducks, geese, swans, pheasants, pigeons, doves, or ostriches. Preferably, the patient is a male or female human of any age or race.

The term "dyslipidemia", as used herein, refers to an abnormal amount of lipids and lipid proteins in the blood, that is, an amount of lipids that is increased or decreased with respect to normal values. The lipids and lipid proteins may be:

Cholesterol, which in abnormal amounts may cause hypercholesterolemia, including familiar hypercholesterolemia due to a defect on chromosome 19 (19p13.1-13.3), and hypocholesterolemia.

Glycerides, such as triclycerides, which in abnormal amounts may cause hypertriglyceridemia and hypotriglyceridemia.

Lipoproteins, such as LDL and HDL, which in abnormal amounts may cause hyperlipoproteinemia and hypolipoproteinemia The probiotic strain of the invention, due to its capacity to absorb cholesterol, is particularly suited for the treatment of a dyslipidemia characterised by increased levels of lipids or lipid proteins.

Thus, in a particular embodiment the dyslipidemia is hypercholesterolemia. The term "hypercholesterolemia", as used herein, refers to any medical condition wherein blood cholesterol levels are elevated above the clinically recommended levels. For example, if cholesterol is measured using low density lipoproteins (LDLs), hypercholesterolemia may exist if the measured LDL levels are above, for example, approximately 70 mg/dl. Alternatively, if cholesterol is measured using free plasma cholesterol, hypercholesterolemia may exist if the measured free cholesterol levels are above, for example, approximately 200-220 mg/dl.

In another particular embodiment the dyslipidemia is hypertriglyceridemia. The term "hypertriglyceridemia", as used herein, refers to high blood levels of triglycerides. Based on fasting levels, mild and moderate hypertriglyceridemia is diagnosed with triglyceride levels of 150-999 mg/dl, and severe and very severe hypertriglyceridemia is diagnosed with triglyceride levels superior to 1,000 mg/dl.

In another particular embodiment the dyslipidemia is hyperlipoproteinemia. The term "hyperlipoproteinemia", as used herein, refers to abnormally elevated levels of any lipoprotein in blood. Lipoproteins include chylomicrons, VLDL, LDL, and IDL. High levels of lipoproteins are associated with atherosclerosis. Hyperlipoproteinemia is divided in the following five types:

Type I: Fat-induced hyperlipidemia or idiopathic familial hyperlipidemia, which is a rare condition caused by deficient or abnormal lipase, characterised by a level of triglycerides of 1,000-10,000 mg/dl and more.

Type II: Familial hyperbetalipoproteinemia and essential familial hypercholesterolemia because of deficient cell surface receptors, characterised by elevated cholesterol and triglycerides, elevated low-density lipoproteins (LDL) and very low-density lipoproteins (VLDL).

Type III: Familial broad-beta disease xanthoma tuberosum caused by a deficient low-density lipoprotein receptor, characterised by elevated cholesterol and triglycerides; elevated intermediate-density lipoproteins.

Type IV: Endogenous hypertriglyceridemia and hyperbetalipoproteinemia with an idiopathic cause, characterised by triglycerides levels lower than 1,000 mg/dL, normal cholesterol, elevated VLDL.

Type V: Mixed hypertriglyceridemia from defective triglyceride clearance, characterised by triglycerides levels higher than 1,000 mg/dL, elevated cholesterol, normal LDL.

Since the various dyslipidemias are involved in insulin resistance, probably due to low blood levels of HDL, the probiotic strain of the invention is also useful in the treatment of insulin resistance or metabolic syndrome.

Thus, in another aspect, the invention relates to a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use in the treatment and/or prevention of metabolic syndrome. Alternatively, this aspect may be reformulated to a use of to a probiotic strain selected from *Lactobacillus reuteri* V3401 with accession number CECT 8605 and *Bifidobacterium breve* BT820 with accession number CECT 8606, or a variant of said strain having cholesterol-absorbing capacity for the manufacture of a medicament for the treatment and/or prevention of metabolic syndrome. Alternatively, this aspect may be reformulated to a method for the treatment and/or prevention of metabolic syndrome in a subject in need thereof, comprising administering to a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

The term "metabolic syndrome" or "insulin resistance syndrome" or "metabolic syndrome X" or "cardiometabolic syndrome" or "syndrome X", as used herein, refers to a disorder of energy utilization and storage, diagnosed by a co-occurrence of three out of five of the following medical conditions: abdominal (central) obesity, elevated blood pressure, elevated fasting plasma glucose, hypertriglyceridemia, and low high-density cholesterol (HDL) levels. Metabolic syndrome increases the risk of developing cardiovascular disease, particularly heart failure, and diabetes.

In another aspect, the invention relates to the use of a probiotic strain selected from *Lactobacillus reuteri* V3401 with accession number CECT 8605 and *Bifidobacterium breve* BT820 with accession number CECT 8606, or a variant of said strain having cholesterol-absorbing capacity as a hypocholesterolemic agent.

The term "hypocholesterolemic agent", as used herein, refers to an agent which provokes a reduction in the blood levels of cholesterol.

In another aspect, the invention relates to a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use as a medicament.

In another aspect, the invention relates to a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use in the treatment and/or prevention of a dyslipidemia.

Alternatively, this aspect may be reformulated to a use of a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for the manufacture of a medicament for the treatment and/or prevention of a dyslipidemia. Alternatively, this aspect may be reformulated to a method for the treatment and/or prevention of a dyslipidemia in a subject in need thereof, comprising administering a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

In another aspect, the invention relates to a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use in the treatment and/or prevention of metabolic syndrome. Alternatively, this aspect may be reformulated to a use of a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for the manufacture of a medicament for the treatment and/or prevention of of metabolic syndrome. Alternatively, this aspect may be reformulated to a method for the treatment and/or prevention of metabolic syndrome in a subject in need thereof, comprising administering a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

In another aspect, the invention relates to the use of a composition comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity as a hypocholesterolemic agent.

The terms "probiotic strain", "*L. reuteri* V3401 with accession number CECT 8605", "*B. breve* BT820 with accession number CECT 8606", "variant", "cholesterol-absorbing capacity", "dyslipidemia", "metabolic syndrome", and "hypocholesterolemic agent" have been described in detail previously and their definitions and embodiments are included here by reference.

In another aspect, the invention relates to a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use as a medicament.

In another aspect, the invention relates to a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use in the treatment and/or prevention of a dyslipidemia.

Alternatively, this aspect may be reformulated to a use of a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for the manufacture of a medicament for the treatment and/or prevention of a dyslipidemia. Alternatively, this aspect may be reformulated to a method for the treatment and/or prevention of a dyslipidemia in a subject in need thereof, comprising administering a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

In another aspect, the invention relates to a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for use in the treatment and/or prevention of metabolic syndrome. Alternatively, this aspect may be reformulated to a use of a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity for the manufacture of a medicament for the treatment and/or prevention of of metabolic syndrome. Alternatively, this aspect may be reformulated to a method for the treatment and/or prevention of metabolic syndrome in a subject in need thereof, comprising administering a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

In another aspect, the invention relates to the use of a feed or nutritional product comprising a probiotic strain selected from *Lactobacillus reuteri* V3401 with accession number CECT 8605 and *Bifidobacterium breve* BT820 with accession number CECT 8606, or a variant of said strain having cholesterol-absorbing capacity as a hypocholesterolemic agent.

The terms "probiotic strain", "*L. reuteri* V3401 with accession number CECT 8605", "*B. breve* BT820 with accession number CECT 8606", "variant", "cholesterol-absorbing capacity", "dyslipidemia", "metabolic syndrome", and "hypocholesterolemic agent" have been described in detail previously and their definitions and embodiments are included here by reference.

Pharmaceutical Products

The person skilled in the art will immediately appreciate that the probiotic strain of the invention is particularly useful as part of a pharmaceutical product. Thus, in another aspect, the invention relates to a pharmaceutical product comprising a therapeutically effective amount of a probiotic strain selected from *Lactobacillus reuteri* V3401 with accession number CECT 8605 and *Bifidobacterium breve* BT820 with accession number CECT 8606, or a variant of said strain having cholesterol-absorbing capacity.

The terms "probiotic strain", "*L. reuteri* V3401 with accession number CECT 8605", "*B. breve* BT820 with accession number CECT 8606", "variant", and "cholesterol-absorbing capacity", have been described in detail in the context of the probiotic strain of the invention, and their definitions and embodiments are included here by reference.

The term "therapeutically effective amount", as used herein, refers to the amount of the probiotic strain of the invention required to achieve a prevention, cure, delay, reduce the severity of, or amelioration of one or more noticeable symptoms of a dyslipidemia, insulin resistance or metabolic syndrome. The terms dyslipidemia, insulin resistance and metabolic syndrome have been described in detail in the context of the therapeutic uses of the invention, and its definition and particularities are also included here by reference. The therapeutically effective amount of a probiotic strain according to the invention may be determined by methods that are conventional in the art.

In a particular embodiment, the pharmaceutical product comprises a mixture of probiotic strains of the invention.

Preferably, the pharmaceutical product comprises at least 2, at least 3, at least 4, or more of the strains of the invention, and wherein each of the strains is represented in the composition in a proportion from 0.1% to 99.9%, preferably from 1% to 99%, more preferably from 10% to 90%. In another embodiment, the composition comprises any of the bacterial strains of the invention together with another strain or mixture of strains and where each of the strains is represented in the composition in a proportion from 0.1% to 99.9%, preferably from 1% to 99%, more preferably from 10% to 90%. In another embodiment, the invention provides a pharmaceutical product which comprises a supernatant of a culture of one or more of the strains according to the invention. Preferably, the supernatant is represented in the pharmaceutical product in a proportion from 0.1% to 99.9%, more preferably from 1% to 99% and even more preferably from 10% to 90%.

In a particular embodiment, the pharmaceutical product comprises a mixture of probiotic strains of the invention.

The pharmaceutical products or compositions provided by the present invention can be administered to a subject for treating a dyslipidemia, insulin resistance or metabolic syndrome. The terms dyslipidemia, insulin resistance and metabolic syndrome have been described in detail in the context of the therapeutic uses of the invention, and its definition and particularities are also included here by reference.

In another particular embodiment, the pharmaceutical product or composition further comprises one or more carriers, excipients, or pharmaceutically acceptable solvents.

The term "pharmaceutically acceptable carrier" or "pharmaceutically acceptable solvent" or "pharmaceutically acceptable excipient", in the context of the present invention, is intended to include any and all solvents, dispersion media, coatings, and antifungal agents, and the like, compatible with pharmaceutical administration. The use of such carriers and vehicles for pharmaceutically active substances is well known in the art, except insofar as any conventional carrier is incompatible with the probiotic strain of the invention. The stabilizers are acceptable carriers, excipients, or solvents which are non-toxic to the subject at the dosages and concentrations employed, and include buffers such as phosphate, citrate, and other organic acids; antioxidants including ascorbic acid and methionine; preservatives (such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight polypeptides (less than about 10 amino acids); proteins such as serum albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, or dextrins; chelating agents such as EDTA; sugars such as sucrose, mannitol, trehalose or sorbitol; forming counterions such as sodium salts; metal complexes (e.g. Zn-protein complexes); and/or nonionic surfactants such as TWEEN™, PLURONICS™ or polyethylene glycol (PEG).

The pharmaceutical products or compositions provided by the present invention can be included in a container, pack, or dispenser together with instructions for administration The pharmaceutical preparation can take the form of tablets, capsules, liquid bacterial suspensions, dried oral supplements, wet oral supplements, dry tube feeding or a wet tube feeding. Preferably the probiotic, the probiotic-containing or supernatant-containing composition and pharmaceutical product is directed to the oral, gastric and/or to the intestinal mucosal surface; however, it could also be directed to nasopharyngeal, respiratory, reproductive or glandular mucosa, and it may be administered to a subject by an oral, nasal, ocular, rectal, topical and/or vaginal route.

The required dosage amount of the probiotic strains in the composition, feed or nutritional product, or pharmaceutical product composition described before will vary according to the nature of the disorder or the proposed use of the composition, and the type of organism involved.

Any suitable dosage of the probiotics or combinations thereof may be used in the present invention provided that the toxic effects do not exceed the therapeutic effects. Therapeutic efficacy and toxicity may be determined by standard pharmaceutical procedures with experimental animals, such as by calculating the $ED$, (the dose therapeutically effective in 50% of the population) or $LD$ (the dose lethal to 50% of the population) statistics. The dose ratio of toxic to therapeutic effects is the therapeutic index, which can be expressed as the $LD/ED$ ratio. Nevertheless, the activity of the new strains in the individual is naturally dose dependent. That is, the more the novel strains are incorporated by means of ingesting or administration of the above food material or the pharmaceutical composition, the higher protective and/or therapeutic activity of the strains. Since the strains of this invention are not detrimental to mankind and animals, a high amount thereof may be incorporated so that essentially a high proportion of the individual's mucosa will be colonized by the novel strains. Compositions which exhibit large therapeutic indices are preferred. The data obtained from animal studies are used to formulate a range of dosage for human or animal use. The dosage contained in such compositions is preferably within a range of circulating concentrations that includes the $ED$, with little or no toxicity. The dosage varies within this range depending upon the dosage form employed, the sensitivity of the patient, and the route of administration. The exact dosage will be determined by the practitioner, in light of factors related to the subject requiring treatment. For instance, for preparing a food composition according to the present invention, the probiotic strain of the present invention is incorporated in a suitable support, in an amount of from $10^5$ cfu/g to about $10^{12}$ cfu/g support material, preferably from about $10^6$ cfu/g to about $10^{11}$ cfu/g support material, more preferably from about $10^6$ cfu/g to about $10^{10}$ cfu/g support material.

In the case of a pharmaceutical product or composition, the dosage of the probiotic strain should be from about $10^5$ cfu/g to about $10^{14}$ cfu/g support material, preferably from about $10^6$ cfu/g to about $10^{13}$ cfu/g support material, more preferably from about $10^7$ cfu/g to about $10^{12}$ cfu/g support material. For the purpose of the present invention the abbreviation cfu shall designate a "colony forming unit" that is defined as the number of bacterial cells as revealed by microbiological counts on agar plates.

Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every day, every 3 to 4 days, every week, or biweekly depending on the half-life and clearance rate of the particular formulation.

In another embodiment, the invention also refers to a pharmaceutical product or composition of the strains of this invention in a lyophilized, freeze-dried or dried form, which can be obtained by any conventional method known in the art.

In another embodiment of the pharmaceutical product or composition, the probiotic strain or the mixture thereof is in the form of non-viable cells.

Biological Material Deposits

A deposit of *Lactobacillus reuteri* V3401 on solid agar medium was made on May 14, 2014, with the Type Culture Spanish Collection, CECT), located at Edificio 3 CUE, Parc Cientific Universitat de Valencia, Catedrático Agustin Escardino 9, 46980 Paterna, Spain, under the conditions stipulated in the Budapest Treaty, and assigned CECT Accession number 8605.

A deposit of *Bifidobacterium breve* BT820 on solid agar medium was made on May 14, 2014, with the Type Culture Spanish Collection, CECT), located at Edificio 3 CUE, Parc Cientific Universitat de Valencia, Catedrático Agustin Escardino 9, 46980 Paterna, Spain, under the conditions stipulated in the Budapest Treaty, and assigned CECT Accession number 8606.

The above deposits were made pursuant to the terms of the Budapest Treaty, and are intended to meet the requirements of 37 CFR § 1.801-1.809. Access to the seed deposits will be available upon request during the pendency of the application to the Commissioner of Patents and Trademarks and persons determined by the Commissioner to be entitled thereto. All restrictions upon availability to the public will be irrevocably removed upon granting of the patent. The deposit will be maintained in the CECT Depository, which is a public depository, for a period of 30 years, or 5 years after the most recent request, or for the enforceable life of the patent, whichever is longer. The viability of the deposit will be tested and will be replaced if it becomes nonviable during that period. Upon allowance of any claims in the application, Applicant will maintain and will make this deposit available to the public, pursuant to the Budapest Treaty.

The following examples serve to illustrate the invention and should not be considered as limiting the scope thereof.

EXAMPLES

Materials and Methods
Bacterial Strains and Growth Conditions

*Lactobacillus reuteri* V3401 and other *Lactobacillus* species were routinely cultured in MRS medium (Oxoid) at 37° C. under anaerobic conditions. *Bifidobacterium breve* BT820 and other bifidobacteria were grown in MRS-cysteine (0.1% p/v) medium also at 37° C. and anaerobically. Cell suspensions for inactivation procedures and for activity assays were grown in standard growth media in Biostat B 5 L fermentors (B. Braun) for 8-24 h. In particular, medium A and medium B at different pH were used. Biomass was concentrated (10×) by centrifugation at 8,000 g and stored at −20° C. until its use.

The ability of *L. reuteri* V3401 to grow using different carbon sources was tested using the API 50 CH test (Biomerieux) following the supplier's instructions. The fermentation strips were analyzed at 24 and 48 h of incubation.

Procedures for Bacteria Inactivation

When samples of inactivated bacteria were prepared, the following procedures were carried out: Heat-inactivation was performed in a standard laboratory autoclave at 120° C. for 20 min. Microwave inactivation was accomplished by using a Milestone Ethos One apparatus in which the bacterial samples were subjected to a 3 min power ramp, up to 300 W, and a final 5 min incubation at this power value. Inactivation by pressure was performed by 15-20 pulses/min for 10 min at 1,500-2,000 bar in a Microfluidics M-110P homogenizer. Incubation in 80 mM $H_2SO_4$ for 4 h at 55° C. and the posterior neutralization (until pH is 7) with 10 M NaOH were the conditions for acid inactivation. The same procedure, but using 80 mM NaOH first and 96% $H_2SO_4$ for alkali neutralization, was followed for base inactivation. Chemical inactivation was carried out by incubation of bacterial samples with 1.5% (v/v) $H_2O_2$ or 50% (v/v) ethanol for 1 h at 37° C. Chemical agents were eliminated by enzymatic treatment with catalase or evaporation respectively.

Enterocytes Cultures

HT-29 enterocytes were obtained from the CIC of the University of Granada (Spain) and cultured in DMEM medium supplemented with a 10% (v/v) of FBS, non-essential amino acids and 2 mM L-glutamine; at 37° C. and 5% (v/v) $CO_2$. Cultures for fluoresterol absorption were grown for 14 days using 96-well plates, incubated for 3-4 h with micelles of fluoresterol and bacterial suspensions at $5·10^8$ bacteria/mL, or 150 µM Ezetimibe (MSD-SP Ltd) as positive control. Before fluorocytometric assays, HT-29 cultures were disaggregated by trypsin treatment, the medium and free micelles of fluoresterol removed by centrifugation and enterocytes suspended in PBS buffer.

Fluoresterol Absorption Analysis

Micelles of fluoresterol, containing 10 mM sodium taurocholate, 6 mM phosphatidylcholine and 0.2 mM fluoresterol were prepared as described by Sparrow et al. (Sparrow et al., 1999, J Lipid Res 40:1747-57). Fluoresterol absorption by bacteria was analyzed incubating bacterial suspensions ($5·10^8$ bacteria/mL) with micelles (0.1 mg/mL fluoresterol) in PBS buffer at 37° C. After 2 h of incubation, the mixture was centrifuged at 5.000 g for 5 min, supernatant discarded and the bacterial pellet resuspended in 0.1 mL of PBS. This procedure was repeated 3 times to removed free fluoresterol micelles. Finally, bacteria associated fluorescence was determined in a Tecan Genius microplate reader (485 nm excitation, 535 nm emission filters) or in a Beckton Dickinson FACScalibur flow cytometer. When flow cytometry was the technique used, bacteria were also stained with ethidium bromide (10 µg/mL) in borate buffer (20 mM sodium borate; 12 mM EDTA; 0.01% formaldehyde and 0.01 Triton X-100) in order to identify its population (reading fluorescence at 488 nm and 661 nm excitation and emission wavelengths respectively). Absorbed fluoresterol was quantified based on the data of fluorescence ($\lambda_{ex}$: 488 nm; $\lambda_{em}$: 530 nm) per cell obtained from 2,000 events in each sample.

Fluoresterol absorbed by HT-29 enterocytes was quantified only by flow cytometry, using the mentioned equipment and the same laser settings but ethidium bromide staining was not necessary to identify the eukaryotic cell population. In each assay, data from negative controls (enterocytes incubated with micelles of fluoresterol) were used as reference to calculate the relative (%) absorption in the problem samples.

Microscopy

Transmission electronic microscopy images of *L. reuteri* V3401 grown in medium A pH 6 and medium B pH 5 media were taken on a Carl Zeiss Libra 120 Plus microscope.

*L. Reuteri* V3401 Protein Extracts and Protein Electrophoresis

Bacterial cells from *L. reuteri* V3401 were resuspended at 0.2 g/mL (wet weight) in ice-cold 50 mM potassium phostate, 1 mM EDTA buffer at pH 6 containing 0.1-0.2 g/mL acid-washed glass beads (0.25-0.5 mm). Physical cell disruption was carried out by agitation in a vortex shaker for ten periods of 20 sec with 20 sec cooling intervals on ice. After centrifugation at 14.000 g for 15 min at 4° C., cell debris was discarded and protein rich supernatant quantified following the Bradford method.

*B. breve* BT820 and other bacteria were incubated ($5 \cdot 10^9$ bacteria/mL) with 0.1-0.2 mg/mL of *L. reuteri* V3401 protein extracts, in 50 mM potassium phosphate buffer pH 6, for 8-12 h at 37° C. in the "activation" experiments. After incubation, protein extract was removed by centrifugation and washing with PBS buffer.

Denaturing SDS-PAGE was performed in 8% (p/v) gels and electrophoretic bands visualized by Coomasie staining. Zymograms for lytic enzymes detection were run in 8% SDS-PAGE semi-native gels containing 10 mg/mL of autoclaved *Micrococcus luteus* cells. After electrophoresis of protein samples (15-20 µg) gels were incubated o/n at 37° C. in 50 mM potassium phostate pH 6 buffer, 0.1% (v/v) Triton X-100. Protein bands with lytic activity were detected by staining with methylene blue (0.1% p/v in 0.01% p/v KOH) for 1-2 min and extensive washing with water.

Bile Salt Hydrolysis Assay

Hydrolysis of bile salts by bacterial samples was assayed as follow: $5 \cdot 10^8$ cfu/mL of bacteria (life) were incubated with 1 mg/mL of porcine bile salts in 1 M borate buffer pH 10 for 2 h at 37° C.: Taurine released by hydrolases was quantified mixing 10 µL of the enzymatic reaction with 100 µL of o-phthalaldehyde (OPA) reagent. Finally, 2 mL of 0.5 M NaOH were added and fluorescence ($\lambda_{ex}$ 340 nm/$\lambda_{em}$ 465 nm) analyzed in a Tecan Genius microplate reader. Taurine concentration was calculated by means of a calibrate curve performed with known concentrations of this organic acid.

Cholesterol Esterase Activity

Cholesterol esterase kinetic was analyzed spectrophotometrically, at 415 nm; for 10 min at 37° C. in a Tecan Genius microplate reader, in order to study if *L. reuteri* V3401 or *B. breve* BT820 were able to inhibit this enzyme. 4-Nitrophenyl butyrate (2.5 mM) was used as chromogenic substrate dissolved in 100 mM sodium phosphate buffer pH 7, 100 mM NaCl, 0.5 mM sodium taurocholate. Bacterial samples ($5 \cdot 10^8$ bacteria/mL) were co-incubated in the reaction mixture with 0.04 U/mL of enzyme and the slope of the straight line ($\lambda_{415\ nm}$ vs time) used to determine and compare the enzymatic activity.

DNA Purification, Amplification and Sequencing

Genomic DNA from bacterial samples was purified using the QIAamp DNA Mini Kit (QIAgen) following the instructions for gram positive bacteria. DNA was used as template in PCR amplification assays for 16S gene purification (QIAquick gel Extraction Kit, QIAgen) and sequencing (Sistemas Genomicos, S.L. Spain), RAPD profiles generation and specific DNA sequences detection. PCR reactions were performed in an Eppendorf Mastercyler® thermocycler, using as primers the oligonucleotides (Eurofins Genomics) present in Table 1 and the reaction components contained in the MasterTaq (5 Prime GmbH) PCR kit. DNA fragments were resolved and visualized by standard agarose gel electrophoresis techniques RNA Isolation and Gene Expression Analysis Prokaryotic and HT-29 enterocytes RNA samples were isolated following the TRIzol method (Chomczynski and Sacchi, 1987, Anal Biochem 162:156-159). Initial biomass samples were obtained from 10 mL cultures at late log-phase for lactobacilli and from 24-well plates (one well per sample) incubated for 14 days for enterocytes. Total RNA samples were incubated with DNase I, and TRIzol extraction was repeated to eliminate the nuclease. RNA concentration, integrity and purity were confirmed by agarose gel electrophoresis and UV spectrophotometry.

For qPCR gene expression studies two-step retrotranscription cDNA synthesis was carried out. First, cDNA was synthesized using oligo d(T)15 and random hexamers as retrotranscription primers, for eukaryotic and prokaryotic RNA samples respectively, and the AffinityScript QPCR cDNA Synthesis Kit (Agilent) following the manufacturer's instructions. In the second step, specific cDNA fragments were amplified in a Stratagene MX3005P thermocycler using SYBR® green (Brilliant III Ultra-Fast SYBR Green, Agilent) as fluorophore. Ct values from control gene (GADPH) reactions and analyzed genes (NPC1L1 or lytic enzyme genes) were used for gene expression calculation, following the ΔΔCt method and the recommendations of Willems et al. (Willems et al., 2008; Anal Biochem 379: 127-9) for data normalization.

Subtractive Hybridization

Bacterial suppressive substractive hybridization (SSH) was performed following the user manuals of the PCR-Select™ cDNA subtraction kit (Clontech Laboratories, Inc., USA), with the exception that random primers was used in the first-strand cDNA synthesis. *L. reuteri* V3401 grown in medium A was used as the tester sample and *L. reuteri* V3401 grown in medium B as the driver in the suppressive substractive hybridization experiment.

The substracted cDNA fragments were cloned into the pGEM-T vector (Promega), amplified using T7 and SP6 oligonucleotides as primers and sequenced by Sistemas Genómicos, S. L (Spain). The obtained nucleotide sequences were identified in the nucleotide database using the Blastn program on the NCBI homepage Animal Groups and Diets Sixty female Wistar rats, weighing approximately 200 g, were purchased from Janvier Labs (France). Rats were individually housed in cages and maintained at constant temperature (23±2° C.) and humidity (55±5%) and exposed to 12-h light/dark cycle.

After 2-week adaptive period on a normal diet (2014 Teklad Global 14% Protein Rodent Maintenance Diet, Harlan), the 60 rats were divided into 6 groups of 10 rats each. The six groups were assigned diets as follows: (A) Control group, with normal diet neither received bacterial samples nor high-cholesterol diet; (B) Positive control, with high-cholesterol diet. The rest of groups were given, in addition to high-cholesterol diet, a daily dose of the bacterial sample ($2 \times 10^9$ bacteria per animal and day) in the drinking water: (C) *L. reuteri* V3401 live; (D) *L. reuteri* V3401 heat-inactivated; (E) *B. breve* BT820 live; (F) *B. breve* BT820 heat-inactivated. The high-cholesterol diet contained 1% (w/w) cholesterol in a standard diet (2014 Teklad Global 14% Protein Rodent Maintenance Diet, Harlan). The rats were fed for 57 days and body weight was recorded. After this period, the rats were euthanized.

Assay for Blood Serum Indexes

Blood samples were collected from the tail vein each 7-10 days in order to determinate the serum cholesterol using the Cholesterol kit from BioSystems. By the end of the experiment period (57 days), after a food deprivation for 12 hours, about 5 mL blood samples from each rat were collected using cardiac puncture. The serum total cholesterol (TCH), high-density lipoprotein cholesterol (HDL-C), low-density lipoprotein cholesterol (LDL-C), triglycerides, phospholipids and glucose were measured with a Mindray BS200 automatic chemical analyzer.

Example 1

Screening of Bacterial Strains with Ability to Inhibit Cholesterol Absorption of Human Enterocytes To carry out this task, a method based on cultures of HT-29 human enterocytes and a fluorescent cholesterol analogue, fluoresterol, was developed.

The absorption of fluoresterol, dissolved in micelles of phosphatidylcholine and sodium taurocholate, by HT-29 enterocytes, can be quantified by flow cytometry. HT-29 cell cultures were incubated in presence of micelles of fluoresterol for at least 3 h, and after culture disaggregation, the fluorescence of the cell population was determined by the mentioned technique. Cell fluorescence is proportional to the amount of absorbed fluoresterol. The method was validated assaying the cholesterol reducing drug Ezetimibe (at a concentration of 150 µM) in the described in vitro model.

The ability of a bacterial collection of more than 400 samples to reduce fluoresterol absorption was determined using this method. Cell cultures were incubated with micelles of fluoresterol and suspensions ($5 \cdot 10^8$ cfu/mL) of viable or inactivated bacteria. The library of non-viable samples was obtained using different methods of inactivation: heat, high pressure, microwaves and incubation with acid, base, alcohol and hydrogen peroxide.

Comparing the average cell fluorescence data of negative control cultures (without bacterial samples) with the values obtained from cultures incubated with bacterial suspensions let us to identify two bacterial species capable to reduce the fluoresterol absorption more than 25%: *Lactobacillus reuteri* V3401 and *Bifidobacterium breve* BT820 (FIG. 1).

Figure 2:
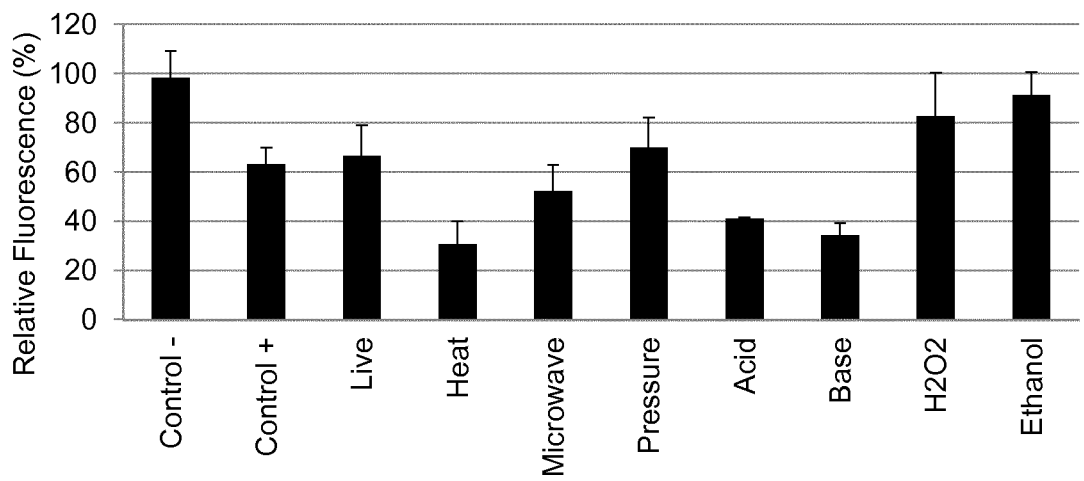
FIG. 2: Relative cell fluorescence average (%) of H-T29 enterocytes incubated with fluoresterol (control −) and with Ezetimibe (control +) or suspensions of inactivated bacteria. A, L. reuteri V3401. B, B. breve BT820.
Figure 2:
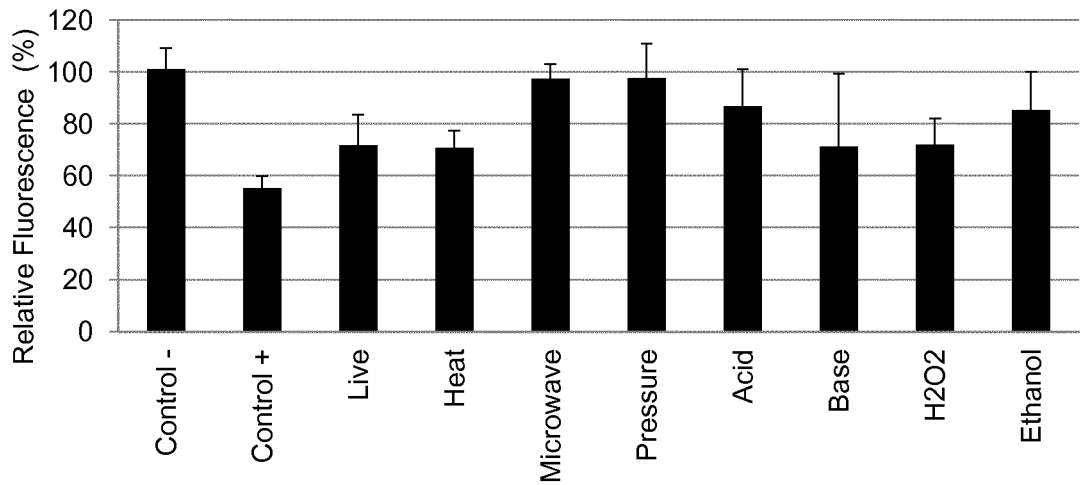

Both bacterial strains showed activity when were assayed live and inactivated by different methods (FIG. 2).

Example 2

Characterization of Bacterial Strains 2.1 *Lactobacillus Reuteri* V3401

*Lactobacillus reuteri* V3401 was isolated from cow raw milk on MRS medium. Its identification was carried out by ribosomic 16S gene amplification and sequencing. The obtained partial ribosomic 16S gene sequence (SEQ ID NO: 1) showed 100% similarity to 16S gene sequences from several EMBL entries corresponding to *L. reuteri* strains (15007, BCS159, NM94-6 and TB-B11).

Figure 3:
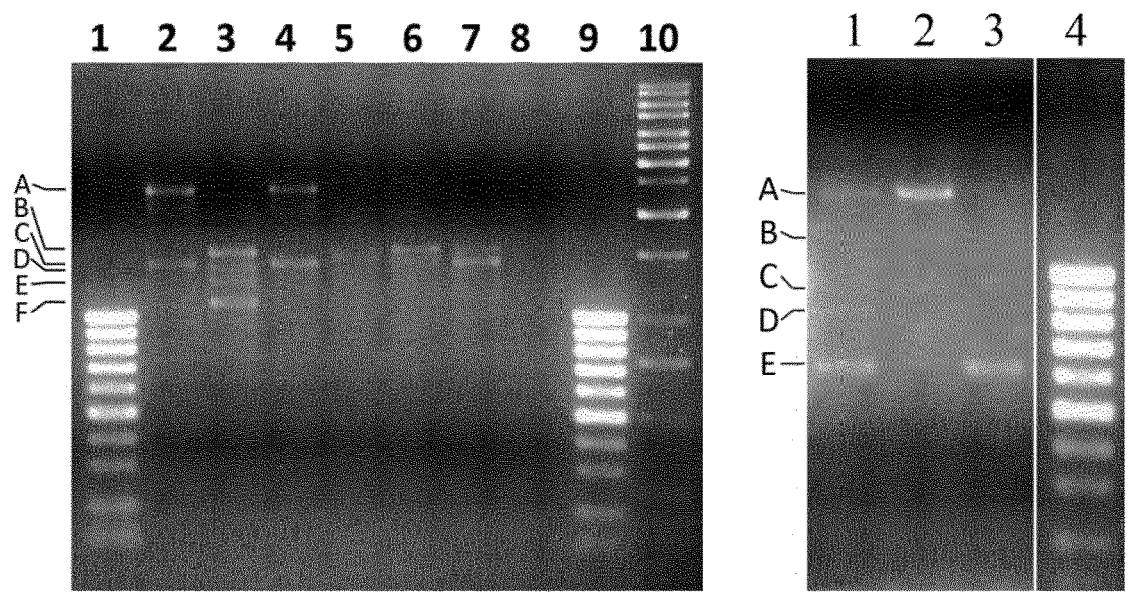
FIG. 3: RAPD patterns of L. reuteri strains generated by (gtg)5 (left panel) and OPL1 (right panel) primers. Left panel: lanes from left to right: lane 1, 100 bp molecular weight marker; lane 2, L. reuteri V3401; lane 3, LR35; lane 4, LR20; lane 5, LR01; lane 6, CECT925; lane 7, DSM 19738; lane 8, no template control (NTC); lane 9, 100 bp molecular weight marker and lane 10, 1 kb molecular weight marker. Right panel: lane 1, V3401; lane 2, LR35; lane 3, LR20; lane 4, 100 bp molecular weight marker.

The differentiation of *L. reuteri* V3401 was carried out with the RAPD (random amplification of polymorphic DNA) fingerprinting test using as template genomic DNA from *L. reuteri* V3401 and five other *L. reuteri* strains (FIG. 3). (gtg)5 and OPL1 oligonucleotides were used as primers (Table 1).

TABLE 1

Oligonucleotides used as primers in PCR assays

| Primers | Target | Sequence (5'-3') |
|---|---|---|
| GAPDHreuExmRNA_D | GAPDH | TGTACTACTAGCTGCTTGGCA (SEQ ID NO: 2) |
| GAPDHreuExmRNA_R | GAPDH | CAGTACGGTTGTTACGCATC (SEQ ID NO: 3) |
| Lysin2_ExmRNA_D | Lytic gene | ATATTCATGAGGCATTTCAAA (SEQ ID NO: 4) |
| Lysin2_ExmRNA_R | Lytic gene | CACGATACTGGGAATGAAAA (SEQ ID NO: 5) |
| (gtg)5 | RAPD | GTGGTGGTGGTGGTG (SEQ ID NO: 6) |
| T7 | pGEM-T | TAATACGACTCACTATAGGG (SEQ ID NO: 7) |
| SP6 | pGEM-T | CGATTTAGGTGACACTATAG (SEQ ID NO: 8) |
| OPL1 | RAPD | GGCATGACCT (SEQ ID NO: 9) |
| H_GAPDH_Fw | Human GAPDH | TGAACGGGAAGCTCACTGG (SEQ ID NO: 10) |
| H_GAPDH_Rw | Human GAPDH | TCCACCACCCTGTTGCTGTA (SEQ ID NO: 11) |
| hNPC1L1 D | Human NPC1L1 | TATGGTCGCCCGAAGCA (SEQ ID NO: 12) |
| hNPC1L1 R | Human NPC1L1 | TGCGGTTGTTCTGGAAATACTG (SEQ ID NO: 13) |

The (gtg)5 and OPL-1 RAPD profiles allowed us to differentiate *L. reuteri* V3401 from the other 5 strains tested. The (gtg)5 band pattern primer was specific of V3401 and LR20 *L. reuteri* strains, being necessary an additional RAPD analysis, with the OPL-1 primer to differentiate between V3401 and LR20 *L. reuteri* strains.

In addition, *L. reuteri* V3401 was characterised based on its biochemical profile using the API CH50 carbohydrate fermentation test (BioMerieux). The results are shown in the Table 2.

TABLE 2

Carbohydrate fermentation profile showed by *L. reuteri* V3401 after 24 h and 48 h incubation, tested with the API CH 50 system.

| | Incubation | |
|---|---|---|
| Carbohydrate | 24 h | 48 h |
| Glycerol | − | − |
| Erythritol | − | − |
| D-Arabinose | − | − |
| L-Arabinose | − | − |
| D-Ribose | − | − |
| D-Xylose | − | − |
| L-Xylose | − | − |
| D-Adonitol | − | − |
| Metil-D-xilopyranoside | − | − |
| D-Galactose | −/+ | + |

TABLE 2-continued

Carbohydrate fermentation profile showed by *L. reuteri* V3401 after 24 h and 48 h incubation, tested with the API CH 50 system.

| Carbohydrate | Incubation 24 h | Incubation 48 h |
|---|---|---|
| D-Glucose | + | + |
| D-Fructose | − | − |
| D-Mannose | − | − |
| L-Sorbose | − | − |
| L-Rhamnose | − | − |
| Dulcitol | − | − |
| Inositol | − | − |
| D-Mannitol | − | − |
| D-Sorbitol | − | − |
| Methyl-D-mannopyranoside | − | − |
| Methyl-D-glucopryranoside | − | − |
| N-Acetylglucosamine | − | − |
| Amygdalin | − | − |
| Arbutin | − | − |
| Esculin | − | − |
| Salicin | −/+ | + |
| D-Cellobiose | − | − |
| D-Maltose | + | + |
| D-Lactose | + | + |
| D-Melibiose | + | + |
| D-Saccharose | + | + |
| D-Trehalose | − | − |
| Inulin | − | − |
| D-Melezitose | − | − |
| D-Raffinose | + | + |
| Amidon | − | − |
| Glycogen | − | − |
| Xylitol | − | − |
| Gentiobiose | − | − |
| D-Turanose | − | − |
| D-Lyxose | − | − |
| D-Tagatose | − | − |
| D-Fucose | − | − |
| L-Fucose | − | − |
| D-Arabitol | − | − |
| L-Arabitol | − | − |
| Potassium gluconate | − | − |
| Potassium 2-Ketogluconate | − | − |
| Potassium 5-Ketogluconate | − | − |

2.2. *Bifidobacterium Breve* BT820

This microorganism was isolated from human breast milk on MRS-cystein agar medium. *Bifidobacterium breve* BT820 was identified at species level by ribosomic 16S gene amplification and sequencing. The obtained partial ribosomic 16S gene sequence (SEQ ID NO: 14) revealed significantly similarity (between 98.6-100%) with 16S gene sequences from several *B. breve* strains (BR2, BGM6, 689b, 875 and JCM1273) deposited in the EMBL DNA database.

Figure 4:
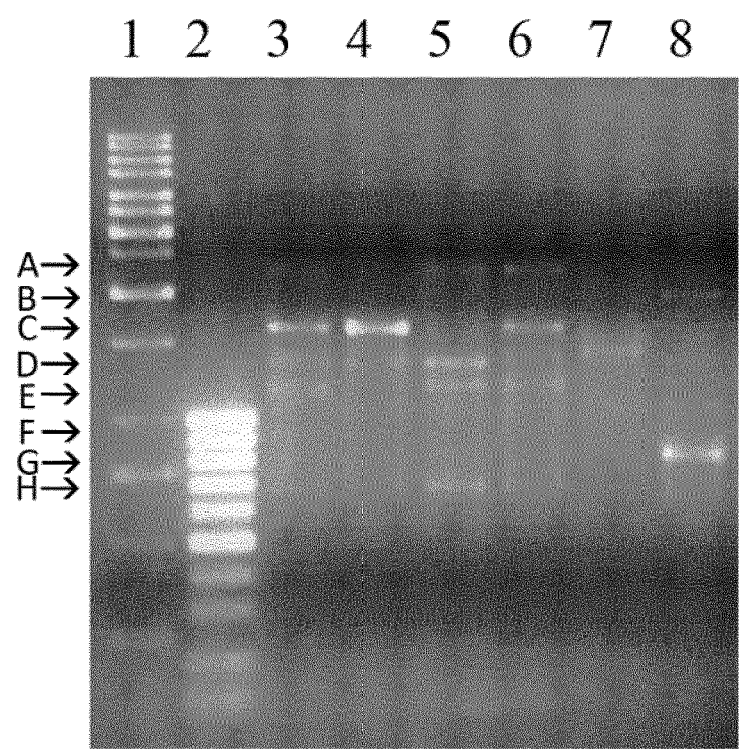
FIG. 4: (gtg)5 RAPD fingerprint from B. breve BT820 and other B. breve strains and a Bifidobacterium longum strain. Lane 1, molecular size marker 1 kb. Lane 2, molecular size marker 100 bp. Lane 3, B. breve BT820. Lane 4, BB26. Lane 5, DSM20091. Lane 6, CECT4839. Lane 7, BB69. Lane 8, B. longum ATCC15707.

In the same way as *L. reuteri* V3401, further analysis was carried out to distinguish *B. breve* BT820 from bacterial strains belonging to the same species or genus. A RAPD fingerprinting test was carried out using genomic DNA from *B. breve* BT820, four *B. breve* strains and a *B. longum* strain, employing the (gtg)5 oligonucleotide as primer. Our results, showed in the FIG. 4 and Table 3, demonstrated that *B. breve* BT820 can be differentiated from others *Bifidobacterium* strains based on its specific (gtg)5 RAPD profile.

TABLE 3

DNA fragments detected in the (gtg)5-RAPD assay carried out with *Bifidobacterium* strains.

| Fragments | BT820 | BB26 | DSM20091 | CECT4839 | BB69 | ATCC15707 |
|---|---|---|---|---|---|---|
| A | ✓ |  | ✓ | ✓ |  |  |
| B |  |  |  |  | ✓ |  |
| C | ✓ | ✓ |  | ✓ |  |  |
| D | ✓ | ✓ | ✓ |  | ✓ | ✓ |
| E | ✓ |  | ✓ | ✓ |  |  |
| F |  |  |  |  |  |  |
| G |  |  |  |  |  | ✓ |
| H | ✓ | ✓ | ✓ | ✓ |  |  |

Example 3

Mechanism of Action

In order to know how both bacterial strains reduce the fluoresterol absorption in HT-29 enterocytes, several assays were performed. First, it was hypothesized that deconjugation of bile salts might contribute to lower fluoresterol levels. Bile-salt hydrolases are the enzymes responsible for this reaction, and glycine and taurine the products of this hydrolysis. In order to evaluate this enzymatic activity in *L. reuteri* V3401 and *B. breve* BT820, both strains were incubated with bile salt (10 mg/mL) for 2 h and the released taurine determinated. Results showed that neither *L. reuteri* V3401 nor *B. breve* BT820 induced bile salt hydrolysis under our experimental conditions.

Another possibility could be that the fluoresterol is metabolized or degraded by the bacterial strains, causing fluorophore degradation, and explaining that the fluorescence associated to HT-29 cells decreased. *L. reuteri* V3401 and *B. breve* BT820 were incubated with fluoresterol micelles during 24 h and fluorescence was measured at different time intervals. The results demonstrated that the total fluorescence did not decay more than the fluoresterol negative control, without bacterial samples and, therefore, the fluoresterol degradation and/or metabolism hypothesis could be rejected.

Figure 5:
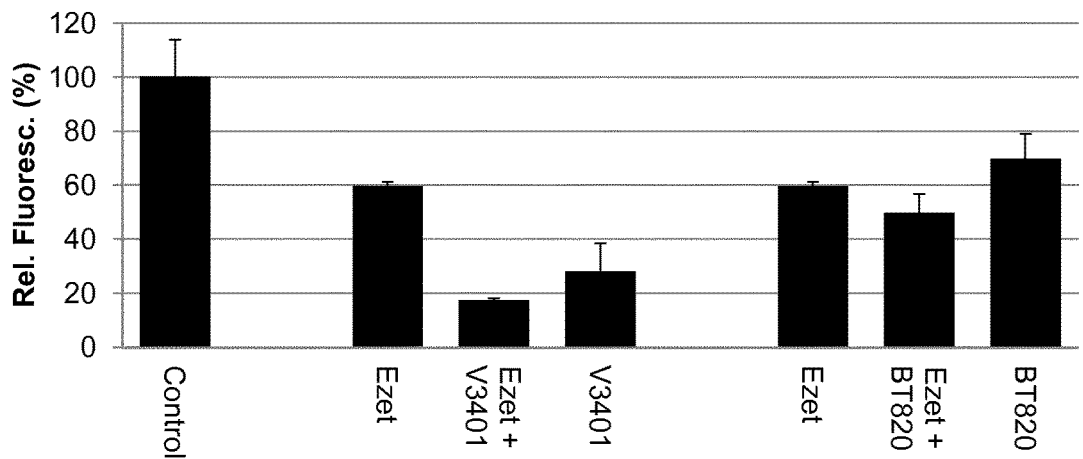
FIG. 5: Relative fluorescence (geometric mean) of HT-29 enterocytes incubated with micelles of fluoresterol (Control), Ezetimibe (300 μM), heat-inactivated cell suspensions ($5 \cdot 10^8$ bacteria/mL) of L. reuteri V3401, B. breve BT820 and enterocytes co-incubated with Ezetime and each microorganism.

*L. reuteri* V3401 and *B. breve* BT820 could inhibit the fluoresterol absorption in HT-29 enterocytes by interaction with the eukaryotic membrane receptor NPC1L1. This receptor seems to be involved in the cholesterol transport through the enterocyte membrane in mammals and it is the molecular target of Ezetimibe. We designed an indirect assay to try to see if *L. reuteri* V3401 and *B. breve* BT820 inhibit the cholesterol transport blocking the NPC1L1 membrane protein. HT-29 enterocytes were incubated with fluoresterol, the bacterial samples and with Ezetimibe at the maximum effective concentration (300 μM) observed in our in vitro model, that induces a 40% inhibition of fluoresterol absorption. We assumed that under these conditions, Ezetimibe completely inhibit the NPC1L1 receptor and will mask the possible effect of the bacteria if its target is the same cholesterol transporter. By contrast, an additive effect of the drug and the bacterial samples could be interpreted as evidence that they act by different mechanisms. Our experimental results showed an increase in the fluoresterol absorption inhibition in those HT-29 cultures incubated with Ezetimibe and *L. reuteri* V3401 or *B. breve* BT820 (FIG. 5). Therefore, we think that both microorganisms do not reduce the fluoresterol absorption blocking the NPC1L1 receptor.

Other possibility is that *L. reuteri* V3401 and *B. breve* BT820 repress the synthesis of NPC1L1 at genetic level. This hypothesis was studied quantifying the relative mRNA concentration in HT-29 enterocytes incubated or not with the bacteria. After RNA purification and retrotrancription, NPC1L1 gene expression was determined by qPCR using the GAPDH gene as reference for data normalization. Our results revealed no changes in the NCP1L1 expression level in HT-29 due to incubation in presence of *L. reuteri* V3401 or *B. breve* BT820.

Pancreatic cholesterol esterase is an enzyme involved in the hydrolysis of cholesterol esters in the digestive tract. This hydrolysis plays an essential role in the regulation of the process of cholesterol absorption. Although this physiologic step could not be responsible of the inhibition of fluoresterol absorption in our HT-29 enterocytes-based in vitro model, we decided to evaluate if *L. reuteri* V3401 and *B. breve* BT820 were able to inhibit this enzyme, since this effect could be involved in the in vivo hypocholesterolemic activity of the strains. The activity of the pancreatic cholesterol esterase was measured spectrophotometrically in presence of bacterial samples and the results showed that the enzyme kinetics do not change with respect to control reactions without bacterial samples.

Figure 6:
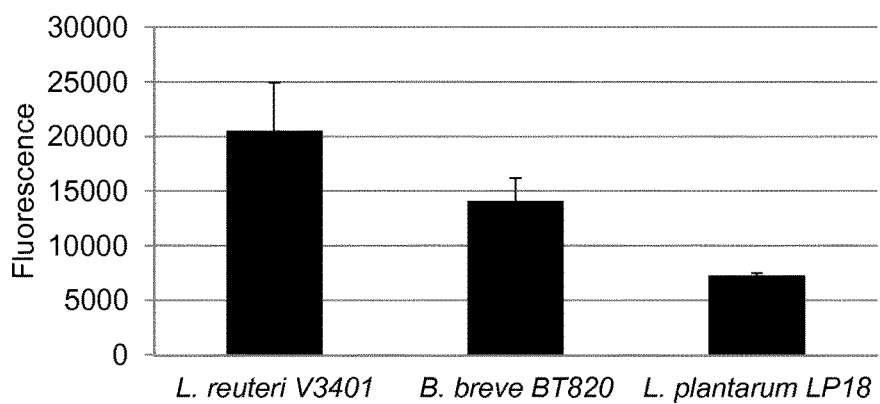
FIG. 6: Net fluorescence (arbitrary units) of samples of L. reuteri V3401, B. breve BT820 and a negative control (randomly selected) incubated with fluoresterol and measured by fluorophotometry.

Three different experiments were performed to study if *L. reuteri* V3401 and *B. breve* BT820 were able to uptake fluoresterol. First, both strains (heat-inactivated) were incubated with micelles of fluoresterol for 3 h and, after extensive washing, the fluorescence associated to bacterial cells determined by fluorospectrophotometry. The results of these assays are showed in FIG. 6.

Figure 7:
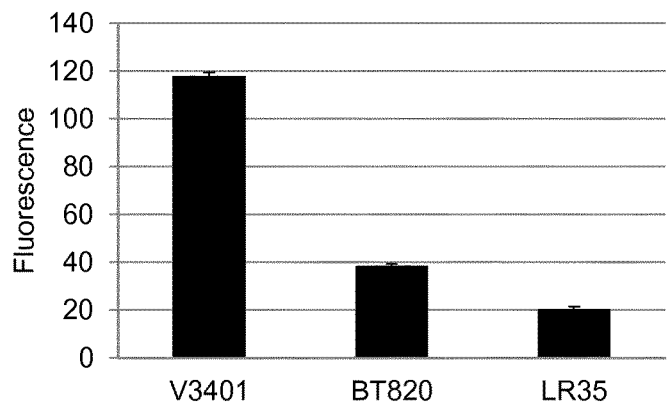
FIG. 7: Fluorescence (geometric mean) per bacteria in suspensions of L. reuteri V3401, B. breve BT820 and a randomly selected negative control, determined by flow fluorocytometry

Our results indicate that *L. reuteri* V3401 and *B. breve* BT820 incorporate fluoresterol into their cells. Bacterial samples from the mentioned strains, treated the same way as previously described, were analysed by flow cytometry obtaining similar results. This technique allows distinguish between fluorescence associated to bacterial cells and fluorescence corresponding to residual micelles of fluoresterol, being thus a more accurate technique. Again, both bacterial strains were able to absorb fluoresterol (FIG. 7).

To confirm the results obtained in previous assays, samples of *L. reuteri* V3401 and *B. breve* BT820, heat-inactivated, and incubated with micelles of fluoresterol were analysed by confocal laser microscopy. The results showed that *L. reuteri* V3401 and *B. breve* BT820 had their cellular structure stained with fluoresterol. The images confirm that both strains are able to uptake fluoresterol and can compete with HT-29 enterocytes in the cellular assays, reducing the fluoresterol available for absorption by the human cells.

Example 4

Figure 8:
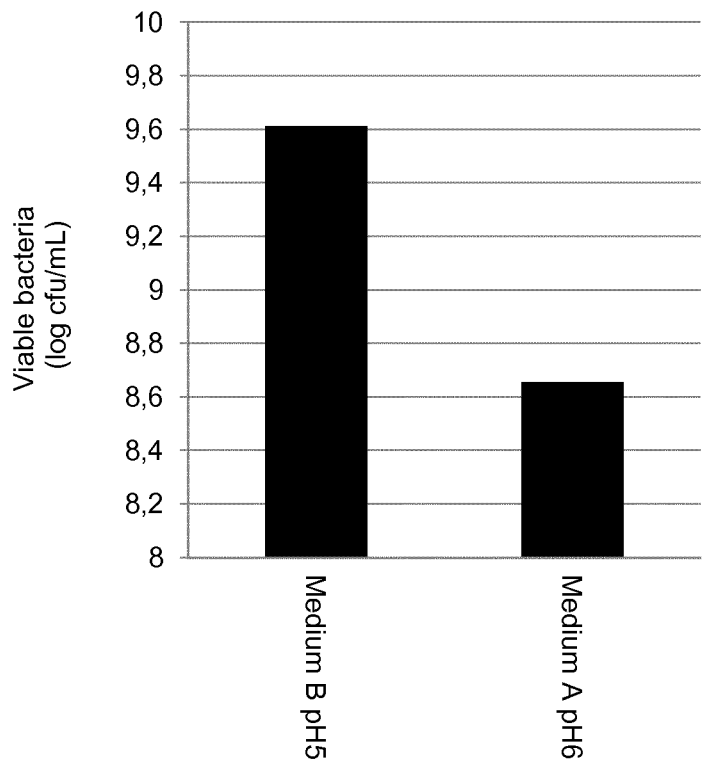
FIG. 8: A, Viable bacteria concentration of L. reuteri V3401 cultures obtained in growth media medium A pH 6 and medium B pH 5. B, Relative cell fluorescence average (%) of H-T29 enterocytes incubated with fluoresterol (control −), Ezetimibe (control +) or suspensions of heat-inactivated L. reuteri V3401 growth under the described conditions.
Figure 8:
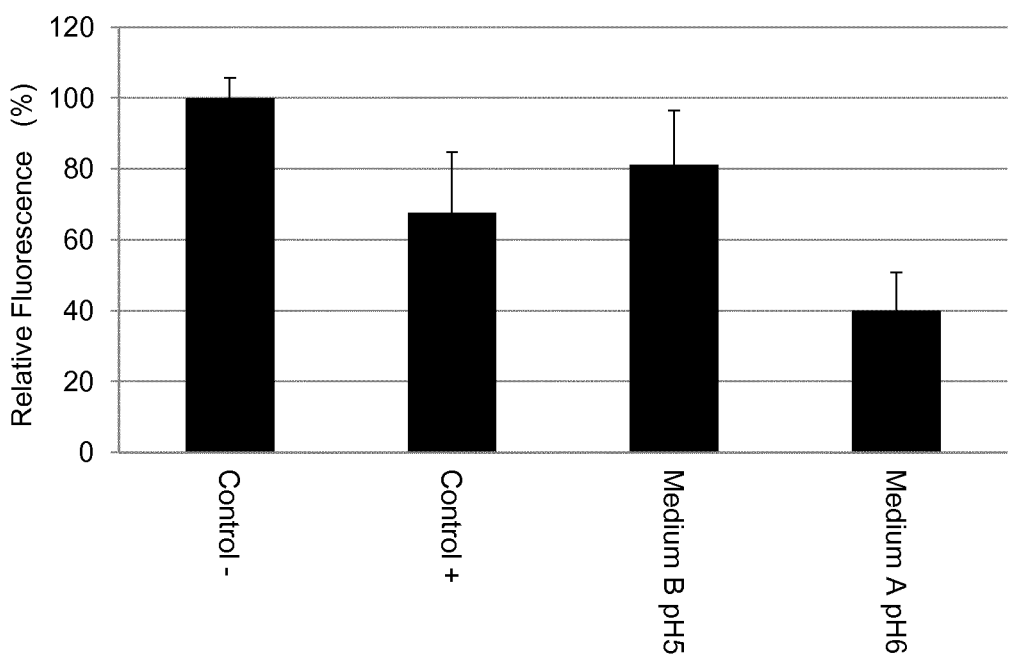

*Lactobacillus Reuteri* V3401 can be Cultured Under Specific Growth Conditions to Increase its Ability to Reduce the Fluoresterol Absorption by Human Enterocytes In the process of optimization of growth conditions of *L. reuteri* V3401 several growth media and physical-chemical variables were assayed, in order to increase the bacterial concentration. *L. reuteri* V3401 samples whose results have been showed were obtained with a growth medium named medium A with a pH adjusted at 6. The results of the optimization experiments allowed the design of a more efficient production process (FIG. 8A) that uses a growth medium named medium B with a pH value of 5. However, after the heat inactivation of the bacterial samples, obtained with the growth process, *L. reuteri* V3401 was unable to reduce the fluoresterol absorption of HT-29 enterocytes cultures, at the same level than samples obtained in medium A at pH 6 (FIG. 8B).

Figure 9:
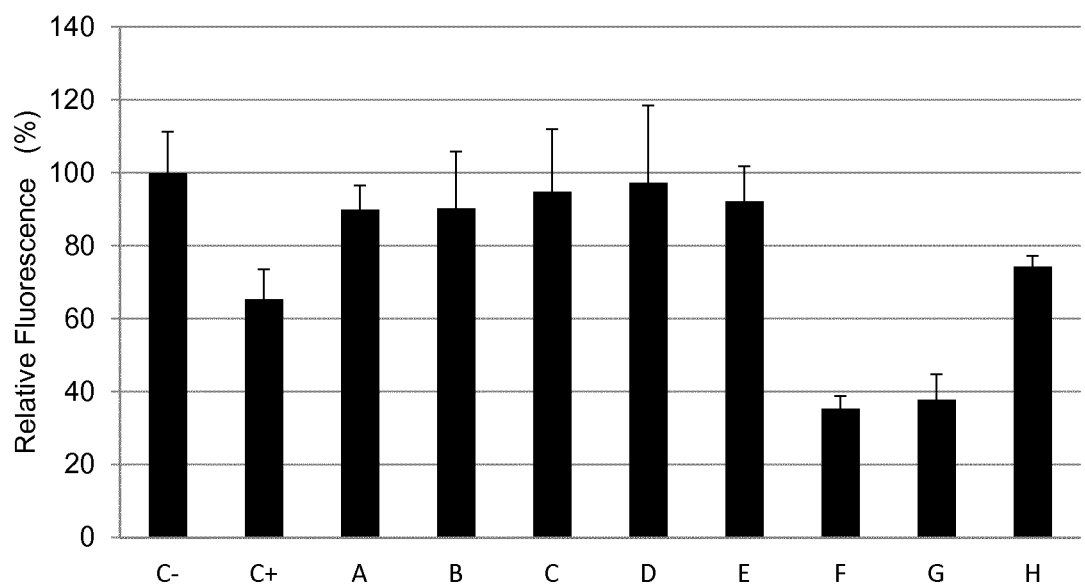
FIG. 9: Relative cell fluorescence average (%) of H-T29 enterocytes incubated with fluoresterol (control −), Ezetimibe (control +) or suspensions of heat-inactivated L. reuteri V3401 grown in different media and growth pH. A, medium B pH 5 plus glucose. B, medium B pH 5 plus potassium phosphate. C, medium B pH 5 low concentration of yeast extract. D, medium B pH 5 plus potassium phosphate and low concentration of yeast extract. E, standard medium B pH 5. F, medium B pH 6. G, medium A pH 6. H, medium A pH 5.

To determine the factor responsible for this change of activity in *L. reuteri* V3401, the effect of the composition of the culture media and the growth pH was studied. Bacterial samples, heat-inactivated, obtained under different growth conditions were tested in HT-29 enterocytes and its ability to reduce the absorption of fluoresterol determined. The results of these tests are shown in FIG. 9.

Figure 10:
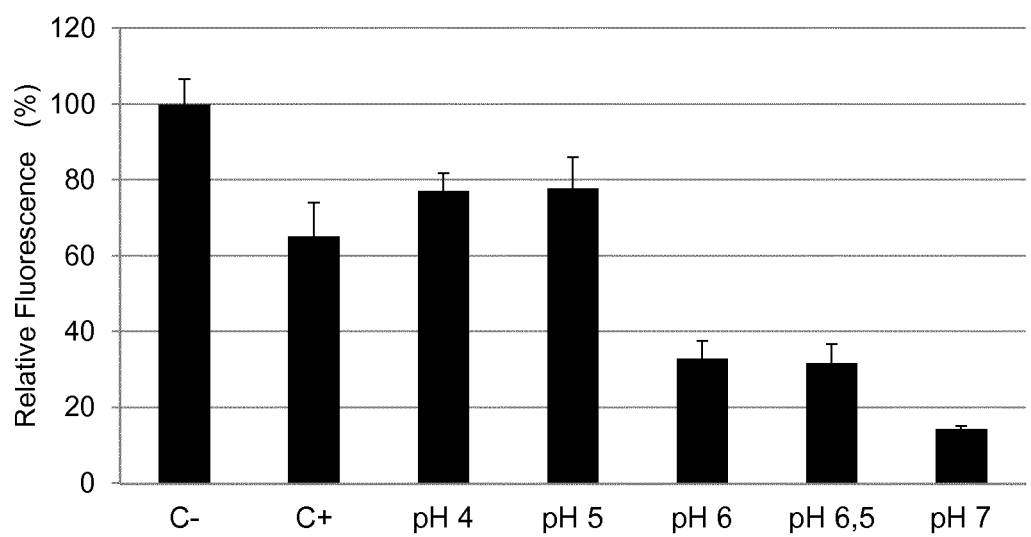
FIG. 10: Relative cell fluorescence average (%) of H-T29 enterocytes incubated with fluoresterol (control −), Ezetimibe (control +) or suspensions of heat-inactivated L. reuteri V3401 grown in medium B at different growth pH values.
Figure 11:
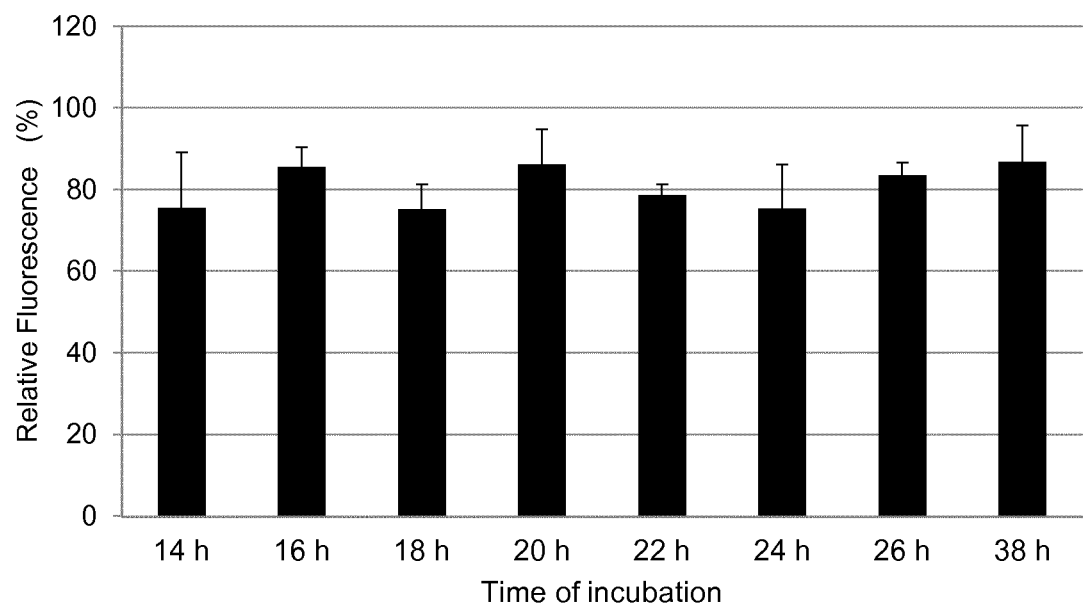
FIG. 11: Relative cell fluorescence average (%) of H-T29 enterocytes incubated with fluoresterol and bacterial suspensions of heat-inactivated L. reuteri V3401 grown in medium B at pH 5 for 14 h, incubated at pH 6 for 24 h and collected at different time intervals.

Ours results seemed to indicate that the extracellular pH could be the key factor in the process of activation of the ability of *L. reuteri* V3401 to reduce fluoresterol absorption in human enterocytes. To confirm this hypothesis, *L. reuteri* V3401 was grown in medium B at different extracellular pH values. Again, once bacterial suspensions were obtained and heat-inactivated, its ability to reduce fluoresterol absorption in HT-29 enterocytes was assayed. The results of this experiment demonstrated that growth pH values equal or greater than 6 increase the ability of *L. reuteri* V3401 to inhibit the fluoresterol uptake in HT-29 human enterocytes (FIG. 10). A new assay was performed, in order to know if extracellular pH could activate *L. reuteri* V3401 in a short period of time. For that, the microorganism was cultured in medium B at pH 5 for 14 h. Then, extracellular pH was changed to 6 for 24 h. Bacterial samples were collected at different time intervals, heat-inactivated and its biological activity tested in HT-29 enterocytes cultures. As it is shown in FIG. 11, *L. reuteri* V3401 grown under the conditions described was unable to reduce fluoresterol absorption in HT-29. These data seem to indicate that the process of activation of *L. reuteri* V3401 requires that the incubation at pH 6 is performed during the active growth phase.

Example 5

Characterization of the Activation Process

In order to study the molecular events responsible of the activation of *L. reuteri* V3401 when grown at pH 6 versus pH 5, a subtractive hybridization assay was performed using cDNA libraries isolated from *L. reuteri* V3401 grown in medium A at pH 6 (tester sample) and from the same strain grown in medium B at pH 5 (driver sample). This experiment was designed to identify those genes overexpressed in the first growth condition.

Figure 12:
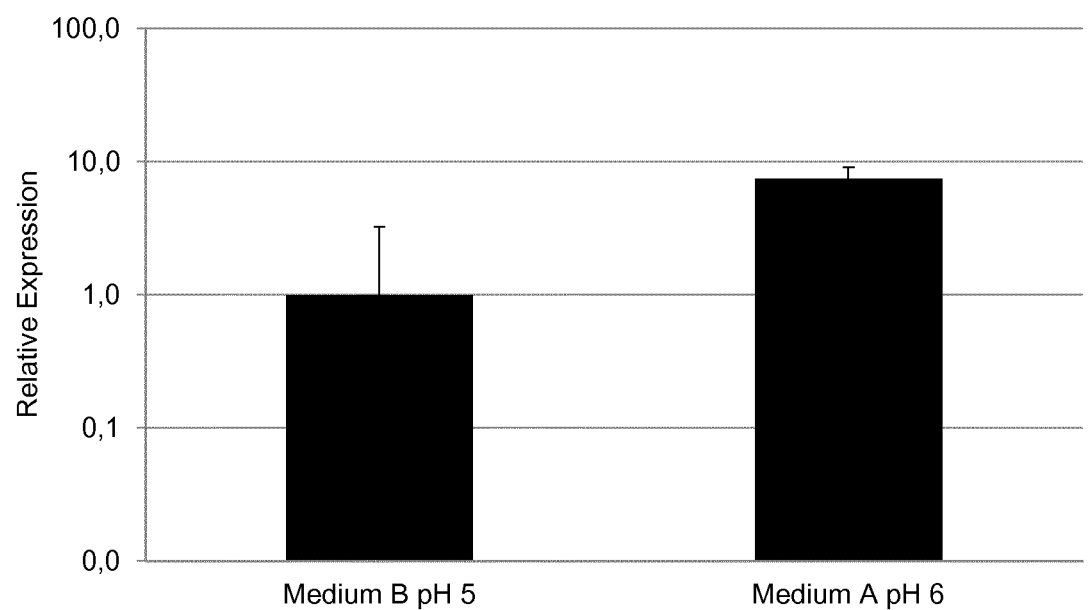
FIG. 12: Relative gene expression values of lytic enzyme in medium B and medium A measured by qPCR.

The results of this experiment allowed the identification of several genes with higher expression level in medium A at pH 6. One of these genes was a lytic enzyme coding gene (sequence similarity-based identification) that could be involved in a process of modification of the *L. reuteri* V3401 cell wall, increasing its affinity and/or permeability toward micelles of fluoresterol. Overexpression of this gene in the medium A at pH 6 was confirmed by qPCR using specific primers (Table 1) and gadph as control for gene expression data normalization (FIG. 12).

Figure 13:
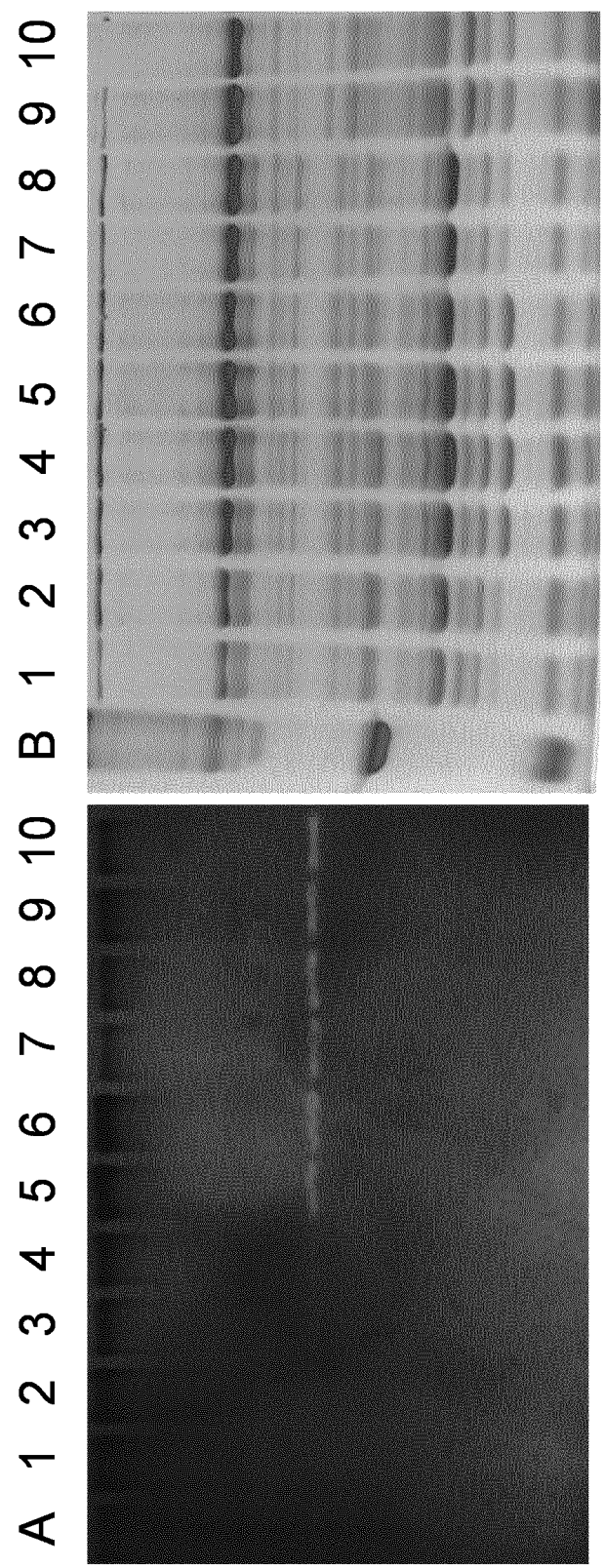
FIG. 13: Zymogram (A) and SDS-PAGE (B) of protein extracts obtained from L. reuteri V3401 grown in medium B at pH 4 (lanes 1-2), pH 5 (3-4), pH 6 (5-6), pH 7 (7-8) and medium A at pH 6 (9-10).

On the other hand, an electrophoretic protein band was identified at the biochemical level in semi-native SDS-PAGE gels (zymograms). Protein extracts were purified from *L. reuteri* V3401, grown in medium B at different pH, and resolved in *Micrococcus luteus* containing SDS-PAGE gels. After methylene blue staining, a lytic enzyme could be detected in those samples obtained from *L. reuteri* V3401 grown at higher pH values (FIG. 13).

It cannot be concluded that the lytic enzyme biochemically identified is encoded by the gene identified in the subtractive hybridization assays, although there is a correlation between the expression of said gene and the enzymatic activity detected in the zymograms.

Figure 14:
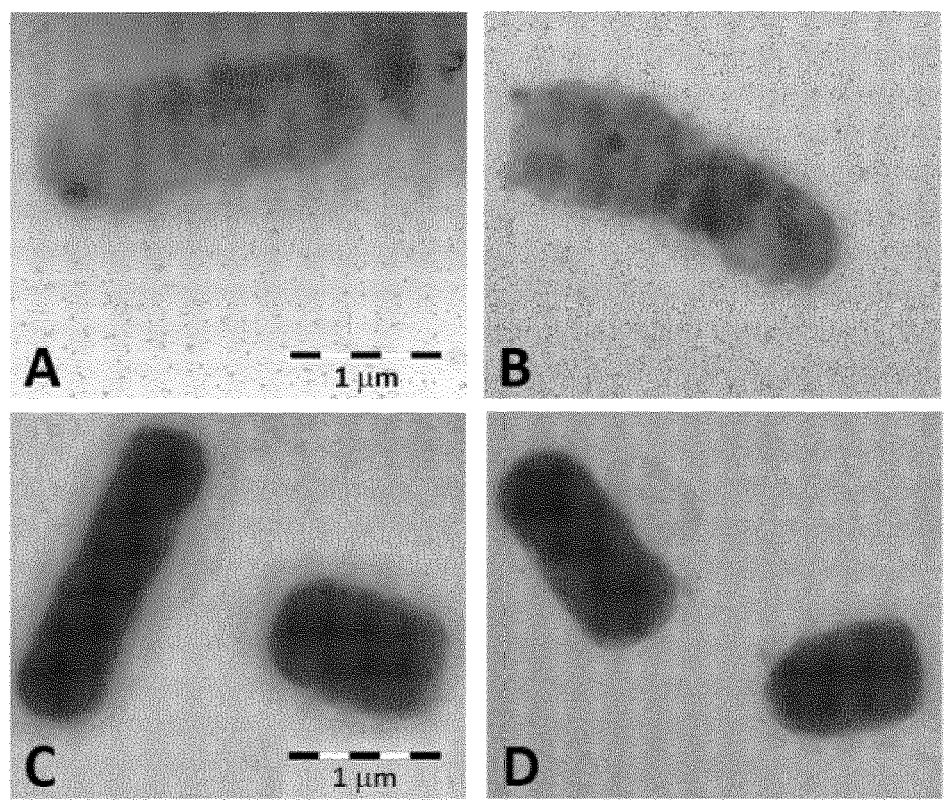
FIG. 14: Transmission electron microscopic images of L. reuteri V3401 grown in medium A at pH 6 (A, B) and medium B at pH 5 (C, D)

These results seem to indicate that the culture of L. reuteri V3401 in medium A or medium B at pH 6, induces the activity of a lytic enzyme that could be implied in the bacterial envelope permeabilization. To study the cell wall integrity, samples of L. reuteri V3401 grown in medium A at pH 6 and in medium B at pH 5 were analyzed by transmission electron microscopy (FIG. 14). The images obtained show bacteria with diffuse cell envelope in samples of L. reuteri V3401 grown in medium A at pH 6 (FIG. 14 A and B) and this could be explained by partial hydrolysis of the cell wall. In contrast, samples of L. reuteri V3401 grown in medium B at pH 5 (FIGS. 14C and D) show more electrodense bacteria with defined shape.

Example 6

Specificity of the Mechanism of Activation

Figure 15:
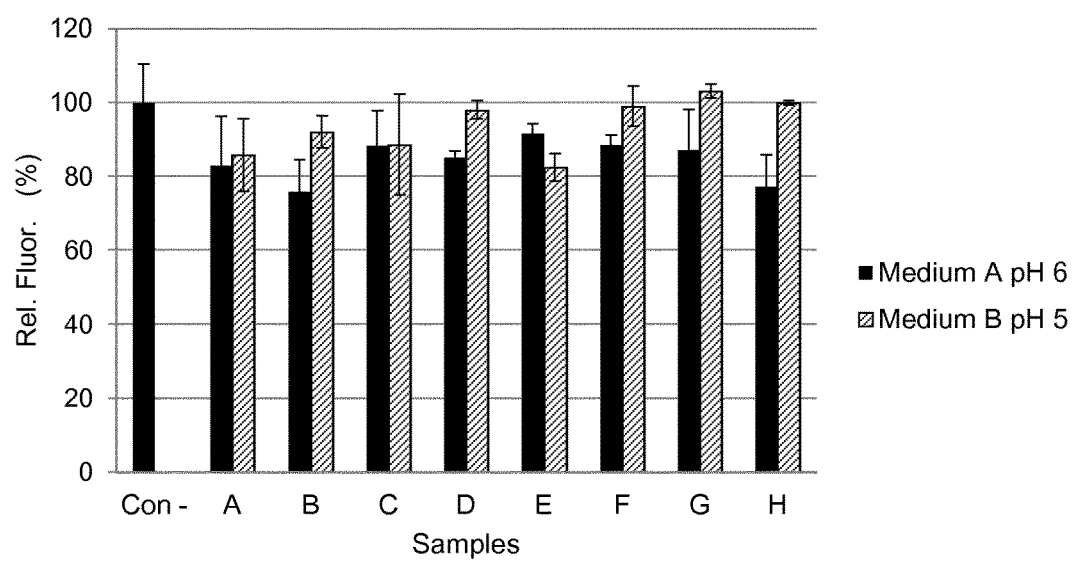
FIG. 15: Relative cell fluorescence average (%) of H-T29 enterocytes incubated with fluoresterol and heat-inactivated bacterial suspensions grown in medium A pH 6 and medium B pH 5 media. A, L. reuteri LR01. B, B. breve BB16. C, L. fermentum CECT5716. D, L. reuteri LR35. E, L. reuteri LR20. F, Lactococcus lactis LL18. F, Leuconostoc mesenteroides LM37. H, Pediococcus pentosaceus PP02.

The influence of culture medium in the fluoresterol uptake activity was analyzed in other bacterial strains, to try to find out how specific could be the effect observed in L. reuteri V3401. First, the activity of several bacterial species grown in medium A at pH 6 and in medium B at pH 5 was analysed with the H-T29 enterocytes assay (FIG. 15).

The results showed that none of the analysed bacteria reduced the fluoresterol absorption in HT-29 enterocytes, regardless the growth medium employed.

As previously mentioned, the activation of L. reuteri V3401 appears to be mediated, at least in part, by an increase in the expression of a lytic enzyme. Furthermore, a gene encoding a lytic enzyme was identified in our experiments of subtractive hybridization and is present in other L. reuteri strains whose genome is published in scientific literature. It was decided to study whether the gene was present in other L. reuteri strains available in our company, using specific primers (Table 1) to perform a PCR experiment using genomic DNA of the L. reuteri mentioned strains. The results indicate that this gene is present in L. reuteri LR20 but not in LR35. These strains showed no ability to reduce the absorption of fluoresterol in our enterocytes assay. It was decided to see if the lytic enzyme gene present in L. reuteri LR20 was actively expressed. Gene expression was quantified by qPCR and the enzyme detected by zymograms, using RNA samples and protein extracts purified from biomass grown in medium A at pH 6 and medium B at pH 5.

Figure 16:
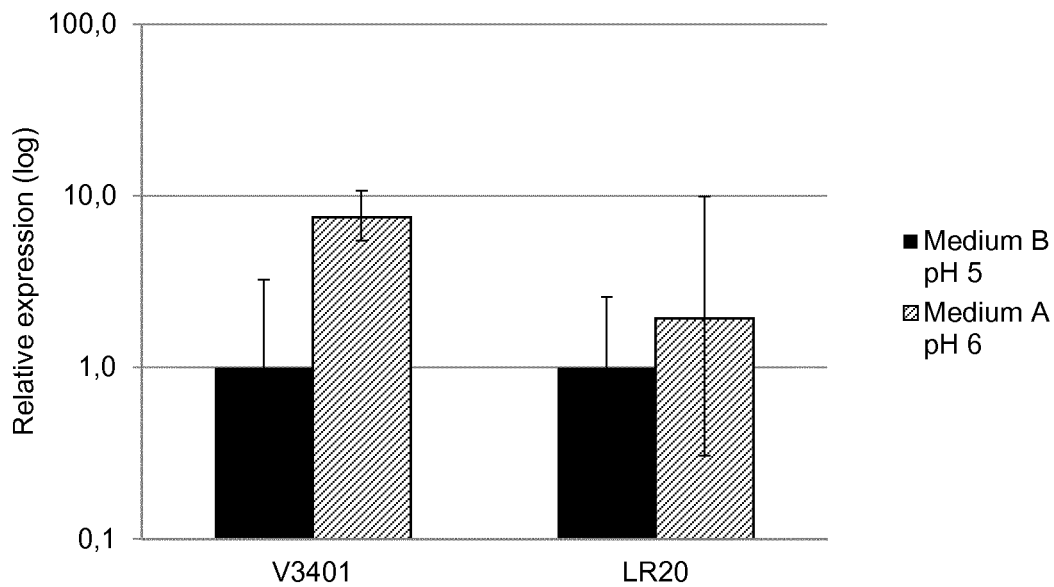
FIG. 16: Relative expression of lytic enzyme gene in L. reuteri V3401 and LR20 strains grown in medium A pH6 and medium B pH5 media quantified by qPCR.

These results show that, unlike in L. reuteri V3401, in L. reuteri LR20 the lytic enzyme gene does not change its expression level depending on the culture medium, being lower than those quantified in L. reuteri V3401 (FIG. 16).

In summary, these data seem to indicate that, although the gene encoding the lytic enzyme is present in other L. reuteri strains, the activation mechanism that improves the fluoresterol uptake of L. reuteri V3401, by means of the lytic enzyme induction, is strain specific.

Example 7

Activation of Other Bacterial Strains

As mentioned above, the optimal growth conditions that enables fluoresterol absorption by L. reuteri V3401, seems to be strain specific. Part of molecular mechanism of this process is based on a lytic enzyme activation which probably digests the cell wall and increases cell permeability. Other bacteria were tested for activation by this enzyme and its fluoresterol absorption capacity assayed.

Figure 17:
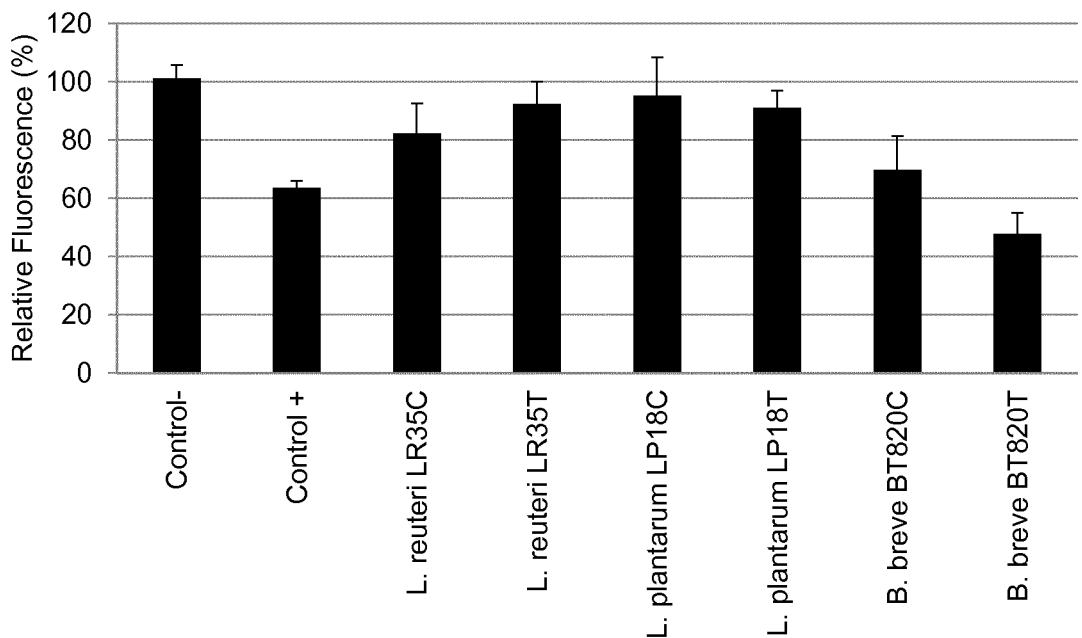
FIG. 17: Relative fluorescence (%) per HT-29 enterocyte incubated with fluoresterol micelles and without bacteria sample (control −), Ezetimibe (control +) and L. reuteri LR35, L. plantarum LP18 and B. breve BT820 suspensions heat-inactivated (C) and incubated with protein extract from L. reuteri V3401 (T).

L. reuteri V3401 protein extract was obtained by growing this microorganism in medium A at pH 6 and incubated with the following bacterial strains: L. reuteri LR35, L. plantarum LP18 and B. breve BT820. After the incubation, bacterial suspensions of these microorganisms were heat-inactivated and tested in the HT-29 fluoresterol absorption assay (FIG. 17). The results showed that neither L. reuteri LR35 nor L. plantarum LP18 reduce fluoresterol absorption in enterocyte cells; untreated or incubated with the protein extract. By contrast, B. breve BT820 confirmed his fluoresterol-lowering ability, detected in previously assays, activity that was higher in bacterial samples incubated with L. reuteri V3401 protein extract (FIG. 17).

Figure 18:
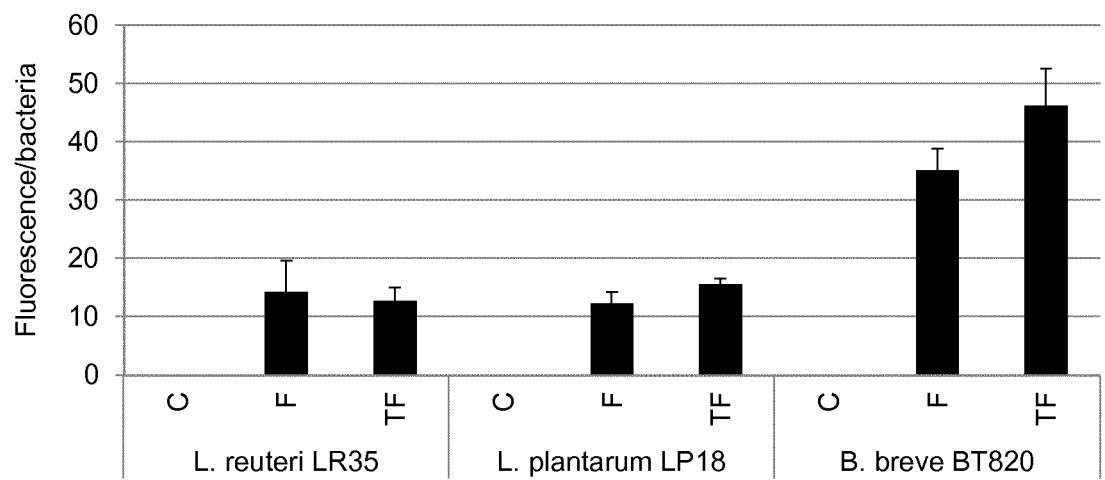
FIG. 18: Fluorescence intensity per cell (Geometric mean) measured by flow fluorocytometry. C: heat-inactivated bacterial samples without fluoresterol (autofluorescence control). F: heat-inactivated bacteria incubated with fluoresterol. TF: bacterial samples treated with L. reuteri V3401 protein extract, heat-inactivated and incubated with fluoresterol micelles.

Uptake of fluoresterol by bacterial suspensions confirmed the results observed in HT-29 cells. Neither L. reuteri LR35 nor L. plantarum LP18 showed fluoresterol absorption ability. Both strains were tested with and without L. reuteri V3401 protein extract incubation. By contrast, B. breve BT820 showed higher fluorescence per cell values in those samples incubated with L. reuteri V3401 protein extract, respect to untreated bacterial samples (FIG. 18)

Example 8

In Vivo Activity in an Animal Model for Hypercholesterolemia

It was decided to test if the L. reuteri V3401 and B. breve BT820 in vitro effect on fluoresterol absorption in human enterocytes could be demonstrated in vivo. To that end, an assay was carried out using an animal model for hypercholesterolemia. The assay consisted in six groups (n=10) of female Wistar rats, weighing approximately 200 g, fed with high cholesterol diet containing 1% (w/w) cholesterol. The bacterial samples were administered ($2 \cdot 10^9$ bacteria per animal and day) in the drinking water (Table 5).

TABLE 5

Animal groups and diets tested in the in vivo assay.

| Group | Animals | Diet | Sample | Dosage (cfu/animal/day) |
|---|---|---|---|---|
| A | 10 | Standard | — | — |
| B | 10 | Standard + 1% cholesterol | — | — |
| C | 10 | Standard + 1% cholesterol | L. reuteri V3401 live | $2 \cdot 10^9$ |
| D | 10 | Standard + 1% cholesterol | L. reuteri V3401 heat-inactivated | $2 \cdot 10^9$ |
| E | 10 | Standard + 1% cholesterol | B. breve BT820 live | $2 \cdot 10^9$ |
| F | 10 | Standard + 1% cholesterol | B. breve BT820 heat-inactivated | $2 \cdot 10^9$ |

Blood samples were collected from the tail vein each 7-10 days; in order to determinate the serum cholesterol. After 57 days, the hypercholesterolemic control group (group B) showed significantly higher serum cholesterol values compared to the group fed with standard diet (control group A). At this moment, the rats were sacrificed and serum total cholesterol (TCH), high-density lipoprotein cholesterol (HDL-C), low-density lipoprotein cholesterol (LDL-C), triglycerides, phospholipids and glucose were measured.

Figure 19:
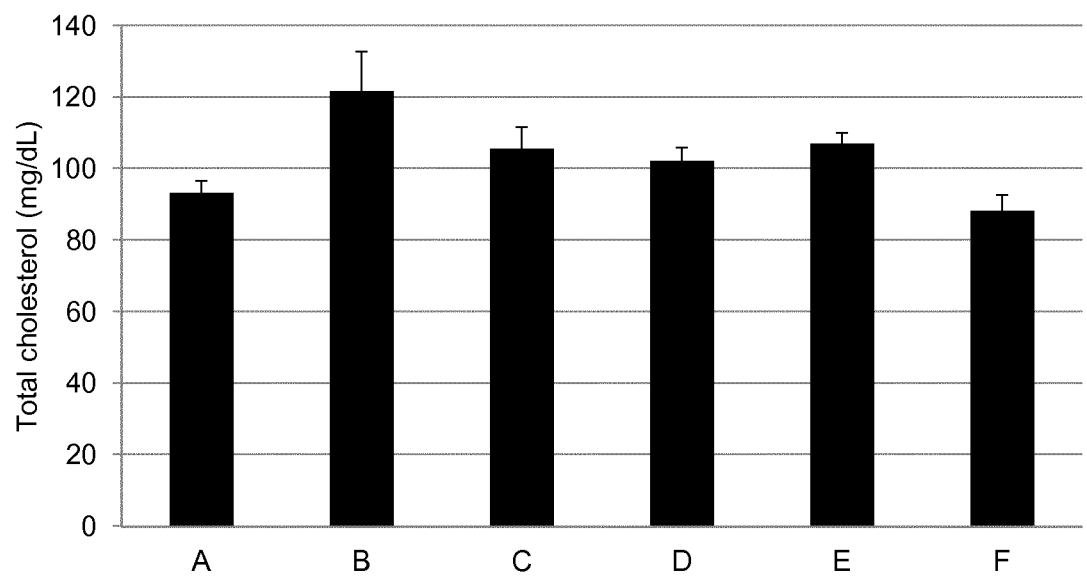
FIG. 19: Serum cholesterol measured in the 6 animal groups, after 57 days. The error bars depicting the standard error of the mean. A, Healthy control group; B, hypercholesterolemic control group; C Live L. reuteri V3401 group; D. Heat.inactivated L. reuteri V3401 group; E, Live B. breve BT820 group; F, Heat-inactivated B. breve BT820 group.

The results showed lower TCH values in the four groups of animals that consumed probiotic samples (FIG. 19). Diet supplementation with any of the four samples was effective in reducing serum cholesterol compared to those fed the same high-cholesterol diet (control group B).

Figure 20:
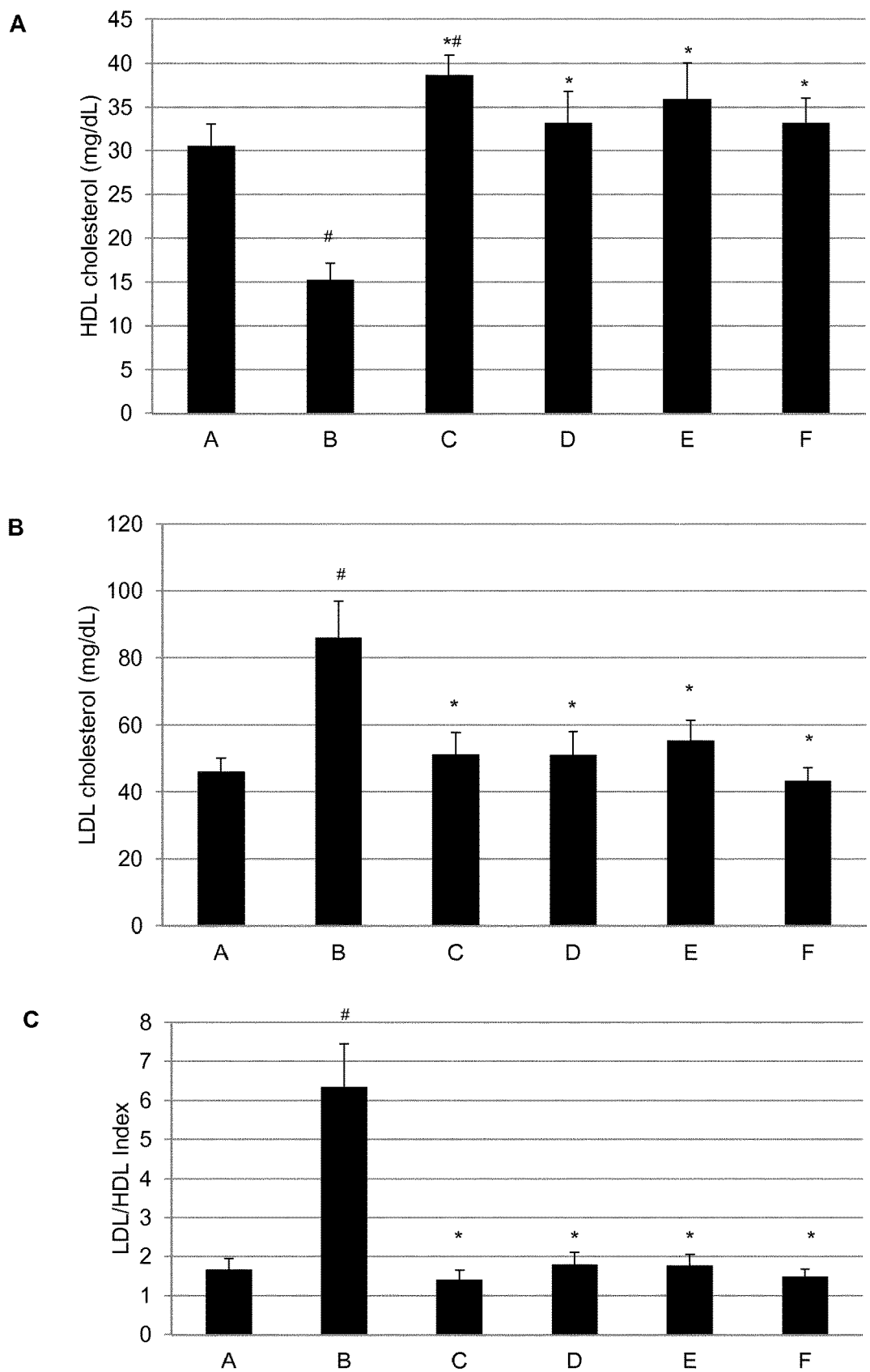
FIG. 20: HDL-cholesterol (A), LDL-cholesterol (B) and LDL-C/HDL-C ratio (C) measured in the six groups of animals, after 57 days. The error bars depicting the standard error of the mean. Significant differences (t Student α=0.05 and p<0.5) respect to the control group A ($^{\#}$) and respect to the hypercholesterolemic group B(*) are indicated.

Moreover, rats fed the high-cholesterol diet and probiotic samples (groups C-F) showed similar HDL-C levels to control group (group A), in contrast to hypercholesterolemic control (group B), which showed significantly decreased levels of HDL-C (FIG. 20A). LDL-C/HDL-C ratio is used to predict cardiovascular risk, being considered more useful than absolute values of serum cholesterol and/or LDL-C. When the LDL-C values (FIG. 20B) were used in order to calculate this ratio (FIG. 20C), the dietary intake of probiotics was confirmed to lower the LDL-C/HDL-C ratio to similar values to health group (group A).

Figure 21:
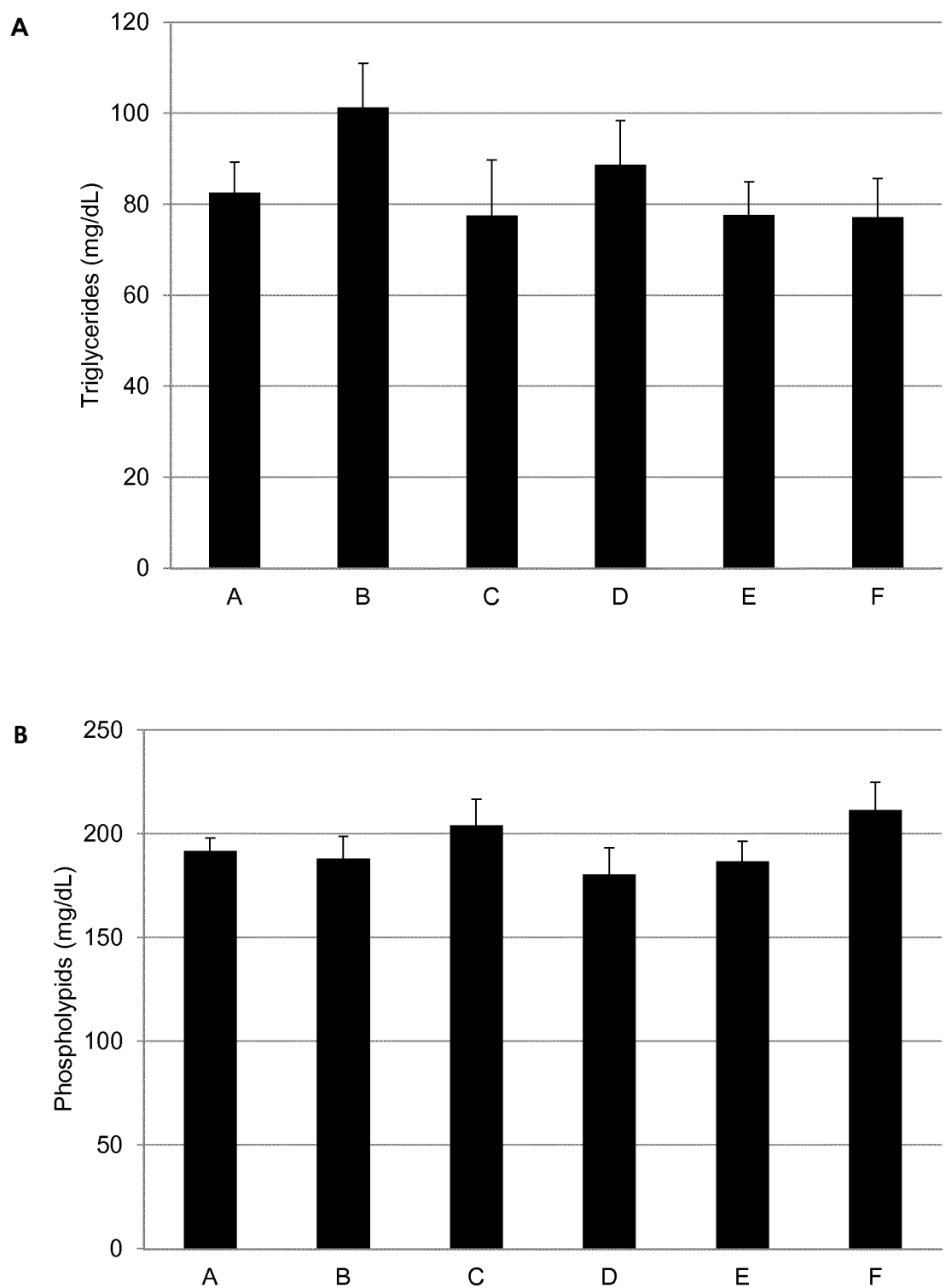
FIG. 21: Plasma triglyceride (A) and phospholipid (B) levels in the 6 animal groups, after 57 days. The error bars depicting the standard error of the mean.

Other parameters studied were the plasma triglyceride and phospholipid levels. The high-cholesterol fed control animals (group B) showed higher values than control group (group A), in contrast to rats fed the high-cholesterol diet and probiotic samples (groups C-F) which showed similar levels of triglycerides to health control group A. However, these differences were no statistic significant (FIG. 21A). Also, no differences were found between the plasma phospholipid levels obtained from the 6 experimental groups (FIG. 21B).

Figure 22:
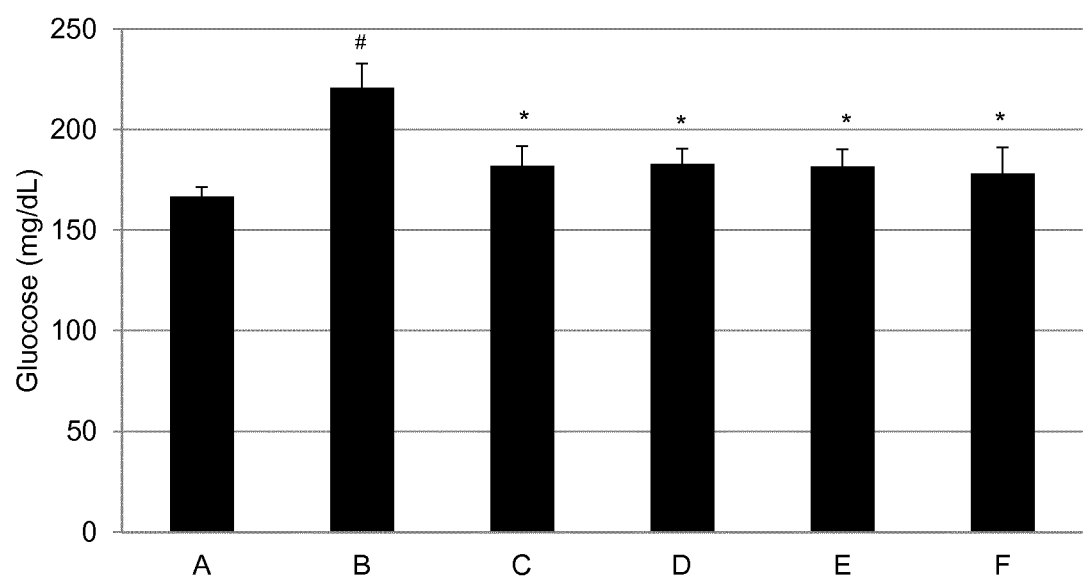
FIG. 22: Plasma glucose values in the 6 animal groups, after 57 days. The error bars depicting the standard error of the mean. Significant differences (t Student α=0.05 and p<0.5) respect to the control group A ($^{\#}$) and to the hypercholesterolemic group B (*) are indicated.

Differences were also observed between the animal group data in a non-lipid parameter. The average plasma glucose level of the high-cholesterol fed rats (group B) was higher than that of health control group (group A). Possibly, this increment is associated with insulin resistance, generally associated with hypercholesterolemia and low HDL-C levels. The 4 animal groups which fed probiotic samples showed glycemic values similar to health control group (group A). This result could be explained by the reversion of the insulin resistance probably promoted by the high HDL-C levels detected in the hypercholesterolemic control group B, and no observed in the probiotic fed groups (FIG. 22).

The invention claimed is:

1. A method for the treatment of a disease or condition selected from the group consisting of dyslipidemia, insulin resistance, and metabolic syndrome,
wherein the method comprises administering to a subject in need of such treatment the probiotic strain *Lactobacillus reuteri* V3401 with accession number CECT 8605.

2. The method according to claim 1, wherein the dyslipidemia is hypercholesterolemia.

3. The method according to claim 1, wherein the probiotic strain is in the form of viable or non-viable cells.

4. The method according to claim 1, wherein the probiotic strain is comprised in a biologically pure culture, a composition, a pharmaceutical product, or a feed or nutritional product;
or wherein a cell membrane, or cell wall-enriched fraction of the probiotic strain, is administered to the subject.

5. The method of claim 1, wherein the probiotic strain has increased cholesterol absorbing capacity and wherein said increased cholesterol absorbing capacity has been obtained by a method comprising a step of inactivating the cells or a step of culturing the cells at a pH between 6 and 9 during their active growth phase.

6. The method according to claim 5, wherein the inactivation is selected from the group consisting of thermal inactivation, microwave inactivation, pressure inactivation, acid inactivation, base inactivation, ethanol inactivation, and peroxide inactivation.

7. The method according to claim 6, wherein the inactivation is thermal inactivation.

8. The method according to claim 5, wherein the pH is 6.

* * * * *

SEQUENCE LISTING

<160> NUMBER OF SEQ ID NOS: 14

<210> SEQ ID NO 1
<211> LENGTH: 700
<212> TYPE: DNA
<213> ORGANISM: Lactobacillus reuteri

<400> SEQUENCE: 1

```
ccccagtcat ctgtcccgcc ttaggcggct ccctccataa tggttaggcc accgactttg      60
ggcgttacaa actcccatgg tgtgacgggc ggtgtgtaca aggcccggga acgtattcac     120
cgcggcatgc tgatccgcga ttactagcga ttccgacttc gtgtaggcga gttgcagcct     180
acagtccgaa ctgagaacgg ctttaagaga ttagcttact ctcgcgagct tgcgactcgt     240
tgtaccgtcc attgtagcac gtgtgtagcc caggtcataa ggggcatgat gatctgacgt     300
cgtccccacc ttcctccggt ttgtcaccgg cagtctcact agagtgccca acttaatgct     360
ggcaactagt aacaagggtt gcgctcgttg cgggacttaa cccaacatct cacgacacga     420
gctgacgacg accatgcacc acctgtcatt gcgtccccga agggaacgcc ttatctctaa     480
ggttagcgca agatgtcaag acctggtaag gttcttcgcg tagcttcgaa ttaaaccaca     540
tgctccaccg cttgtgcggg cccccgtcaa ttccttgag tttcaacctt gcggtcgtac      600
tccccaggcg gagtgcttaa tgcgttagct ccggcactga agggcggaaa ccctccaaca     660
cctagcactc atcgtttacg gcatggacta ccagggtatc                           700
```

<210> SEQ ID NO 2
<211> LENGTH: 21
<212> TYPE: DNA
<213> ORGANISM: Artificial Sequence
<220> FEATURE:
<223> OTHER INFORMATION: GAPDHreuExmRNA_D primer

<400> SEQUENCE: 2

```
tgtactacta gctgcttggc a                                                21
```

<210> SEQ ID NO 3
<211> LENGTH: 20
<212> TYPE: DNA
<213> ORGANISM: Artificial Sequence
<220> FEATURE:
<223> OTHER INFORMATION: GAPDHreuExmRNA_R primer -continued

<400> SEQUENCE: 3
cagtacggtt gttacgcatc                                               20

<210> SEQ ID NO 4
<211> LENGTH: 21
<212> TYPE: DNA
<213> ORGANISM: Artificial Sequence
<220> FEATURE:
<223> OTHER INFORMATION: Lysin2_ExmRNA_D primer

<400> SEQUENCE: 4
atattcatga ggcatttcaa a                                             21

<210> SEQ ID NO 5
<211> LENGTH: 20
<212> TYPE: DNA
<213> ORGANISM: Artificial Sequence
<220> FEATURE:
<223> OTHER INFORMATION: Lysin2_ExmRNA_R primer

<400> SEQUENCE: 5
cacgatactg ggaatgaaaa                                               20

<210> SEQ ID NO 6
<211> LENGTH: 15
<212> TYPE: DNA
<213> ORGANISM: Artificial Sequence
<220> FEATURE:
<223> OTHER INFORMATION: (gtg)5 primer

<400> SEQUENCE: 6
gtggtggtgg tggtg                                                    15

<210> SEQ ID NO 7
<211> LENGTH: 20
<212> TYPE: DNA
<213> ORGANISM: Artificial Sequence
<220> FEATURE:
<223> OTHER INFORMATION: T7 primer

<400> SEQUENCE: 7
taatacgact cactataggg                                               20

<210> SEQ ID NO 8
<211> LENGTH: 20
<212> TYPE: DNA
<213> ORGANISM: Artificial Sequence
<220> FEATURE:
<223> OTHER INFORMATION: SP6 primer

<400> SEQUENCE: 8
cgatttaggt gacactatag                                               20

<210> SEQ ID NO 9
<211> LENGTH: 10
<212> TYPE: DNA
<213> ORGANISM: Artificial Sequence
<220> FEATURE:
<223> OTHER INFORMATION: OPL1 primer

<400> SEQUENCE: 9
ggcatgacct                                                          10

<210> SEQ ID NO 10

```
<211> LENGTH: 19
<212> TYPE: DNA
<213> ORGANISM: Artificial Sequence
<220> FEATURE:
<223> OTHER INFORMATION: H_GAPDH_Fw primer

<400> SEQUENCE: 10
tgaacgggaa gctcactgg                                                19

<210> SEQ ID NO 11
<211> LENGTH: 20
<212> TYPE: DNA
<213> ORGANISM: Artificial Sequence
<220> FEATURE:
<223> OTHER INFORMATION: H_GAPDH_Rw primer

<400> SEQUENCE: 11
tccaccaccc tgttgctgta                                               20

<210> SEQ ID NO 12
<211> LENGTH: 17
<212> TYPE: DNA
<213> ORGANISM: Artificial Sequence
<220> FEATURE:
<223> OTHER INFORMATION: hNPC1L1 D primer

<400> SEQUENCE: 12
tatggtcgcc cgaagca                                                  17

<210> SEQ ID NO 13
<211> LENGTH: 22
<212> TYPE: DNA
<213> ORGANISM: Artificial Sequence
<220> FEATURE:
<223> OTHER INFORMATION: hNPC1L1 R primer

<400> SEQUENCE: 13
tgcggttgtt ctggaaatac tg                                            22

<210> SEQ ID NO 14
<211> LENGTH: 438
<212> TYPE: DNA
<213> ORGANISM: Bifidobacterium breve

<400> SEQUENCE: 14
gggatccagg cagcttgctg cctggtgaga gtggcgaacg ggtgagtaat gcgtgaccga    60
cctgccccat gcaccggaat agctcctgga acgggtggt aatgccggat gctccatcac   120
accgcatggt gtgttgggaa agcctttgcg gcatgggatg ggtcgcgtc ctatcagctt   180 gatggcgggg taacggccca ccatggcttc gacgggtagc cggcctgaga gggcgaccgg   240
ccacattggg actgagatac ggcccagact cctacgggag gcagcagtgg ggaatattgc   300
acaatgggcg caagcctgat gcagcgacgc cgcgtgaggg atggaggcct cgggttgta   360 aacctctttt gttagggagc aaggcacttt gtgttgagtg tacctttcga ataagcaccg   420
gctaactacg tgccagca                                                438
```